United States Patent
Cichocki et al.

(12) 
(10) Patent No.: US 11,684,701 B2
(45) Date of Patent: Jun. 27, 2023

(54) OPERATING ROOM COATING APPLICATOR AND METHOD

(71) Applicant: Ethicon, Inc., Somerville, NJ (US)

(72) Inventors: Frank Richard Cichocki, Easton, PA (US); Duan Li Ou, Warren, NJ (US)

(73) Assignee: Ethicon, Inc., Raritan, NJ (US)

( * ) Notice: Subject to any disclaimer, the term of this patent is extended or adjusted under 35 U.S.C. 154(b) by 0 days.

(21) Appl. No.: 16/697,227

(22) Filed: Nov. 27, 2019

(65) Prior Publication Data

US 2020/0171528 A1 Jun. 4, 2020

Related U.S. Application Data

(60) Provisional application No. 62/773,102, filed on Nov. 29, 2018.

(51) Int. Cl.
*A61L 27/54* (2006.01)
*A61L 2/03* (2006.01)
(Continued)

(52) U.S. Cl.
CPC .............. *A61L 27/54* (2013.01); *A61L 2/03* (2013.01); *A61L 2/07* (2013.01); *A61L 2/20* (2013.01);
(Continued)

(58) Field of Classification Search
CPC . B05B 7/1606; B05B 12/081; B05B 17/0615; A61L 27/54; C23C 14/12
See application file for complete search history.

(56) References Cited

U.S. PATENT DOCUMENTS 3,976,049 A 8/1976 Yamashita
4,057,047 A 11/1977 Gossett
(Continued)

FOREIGN PATENT DOCUMENTS

CN 1827178 A 9/2006
CN 101553359 A 10/2009
(Continued)

OTHER PUBLICATIONS

International Search Report dated Feb. 27, 2020 for Application No. PCT/IB2019/060229.
(Continued)

*Primary Examiner* — Dah-Wei D. Yuan
*Assistant Examiner* — Andrew J Bowman

(57) ABSTRACT

The present disclosure provides a coating applicator operable to apply a coating of a therapeutic agent upon an object comprising an openable and sealable device compartment, a therapeutic agent positioned in communication with the device compartment, an atomizer operable to atomize the therapeutic agent, and a source of vacuum in communication with the device compartment. The coating applicator may further comprise a drier, and the drier may comprise an arrangement to operate the source of vacuum for a time sufficient to promote drying of applied therapeutic agent. Deposition of the atomized therapeutic agent may be promoted by contacting the atomized therapeutic agent while the object is in a chilled condition and by contacting the object with atomized therapeutic agent while the atomized therapeutic agent is in a heated condition. Related methods are also disclosed.

23 Claims, 14 Drawing Sheets

(51) Int. Cl.

| | | |
|---|---|---|
| *A61L 2/07* | (2006.01) | |
| *A61L 2/20* | (2006.01) | |
| *A61L 2/26* | (2006.01) | |
| *A61L 17/00* | (2006.01) | |
| *B05B 7/16* | (2006.01) | |
| *B05B 15/00* | (2018.01) | |
| *A61L 17/14* | (2006.01) | |
| *C09D 7/20* | (2018.01) | |
| *C09D 7/62* | (2018.01) | |
| *A61L 31/10* | (2006.01) | |
| *A61L 31/14* | (2006.01) | |
| *A61L 31/16* | (2006.01) | |
| *C09D 5/14* | (2006.01) | |
| *C09D 183/04* | (2006.01) | |
| *C10M 107/50* | (2006.01) | |
| *B05B 12/08* | (2006.01) | |
| *B05B 17/06* | (2006.01) | |
| *B05D 1/02* | (2006.01) | |
| *B05D 3/04* | (2006.01) | |
| *C10N 40/00* | (2006.01) | |
| *C10N 30/16* | (2006.01) | |
| *C10N 50/08* | (2006.01) | |
| *A61M 11/00* | (2006.01) | |

(52) U.S. Cl.
CPC ............... *A61L 2/26* (2013.01); *A61L 17/005* (2013.01); *A61L 17/145* (2013.01); *A61L 31/10* (2013.01); *A61L 31/14* (2013.01); *A61L 31/16* (2013.01); *B05B 7/1606* (2013.01); *B05B 7/1686* (2013.01); *B05B 12/081* (2013.01); *B05B 15/00* (2013.01); *B05B 17/0615* (2013.01); *B05D 1/02* (2013.01); *B05D 3/0493* (2013.01); *C09D 5/14* (2013.01); *C09D 7/20* (2018.01); *C09D 7/62* (2018.01); *C09D 183/04* (2013.01); *C10M 107/50* (2013.01); *A61L 2202/181* (2013.01); *A61L 2202/182* (2013.01); *A61L 2300/202* (2013.01); *A61L 2300/404* (2013.01); *A61L 2300/606* (2013.01); *A61L 2400/10* (2013.01); *A61L 2420/02* (2013.01); *A61L 2420/04* (2013.01); *A61L 2420/06* (2013.01); *A61M 11/005* (2013.01); *C10M 2229/0445* (2013.01); *C10N 2030/16* (2013.01); *C10N 2040/50* (2020.05); *C10N 2050/08* (2013.01)

(56) References Cited

U.S. PATENT DOCUMENTS

| | | | |
|---|---|---|---|
| 4,940,542 A | 7/1990 | Simizu et al. | |
| 5,046,479 A | 9/1991 | Usui | |
| 5,205,277 A | 4/1993 | Chao-tsung | |
| 5,474,797 A | 12/1995 | Sioshansi et al. | |
| 6,143,370 A * | 11/2000 | Panagiotou | A61L 31/10 |
| | | | 427/255.14 |
| 8,315,700 B2 | 11/2012 | Citron | |
| 8,551,555 B2 * | 10/2013 | Burghard | B82Y 30/00 |
| | | | 427/2.25 |
| 8,790,677 B2 | 7/2014 | Mckay | |
| 8,997,978 B2 | 4/2015 | Stopek | |
| 9,220,294 B2 | 12/2015 | Mccullough | |
| 9,364,215 B2 | 6/2016 | Stopek | |
| 9,688,459 B2 | 6/2017 | Stanley et al. | |
| 9,848,955 B2 | 12/2017 | Buevich | |
| 9,987,400 B1 | 6/2018 | Chen | |
| 10,314,951 B2 | 6/2019 | Chen | |
| 10,517,691 B2 | 12/2019 | Ahrens | |
| 2002/0022762 A1 | 2/2002 | Beane et al. | |
| 2004/0068294 A1 | 4/2004 | Scalzo | |
| 2004/0220614 A1 | 11/2004 | Scalzo | |
| 2005/0034723 A1 | 2/2005 | Bennett et al. | |
| 2005/0181116 A1 | 8/2005 | Worsham | |
| 2005/0188921 A1 | 9/2005 | Malone | |
| 2007/0092494 A1 | 4/2007 | Higgins et al. | |
| 2007/0218197 A1 * | 9/2007 | Kurono | B22D 25/00 |
| | | | 427/230 |
| 2007/0254091 A1 * | 11/2007 | Fredrickson | A61L 27/34 |
| | | | 427/2.24 |
| 2007/0292305 A1 | 12/2007 | Dempsey | |
| 2009/0099532 A1 | 4/2009 | Cuevas | |
| 2009/0169714 A1 | 7/2009 | Burghard et al. | |
| 2010/0021620 A1 * | 1/2010 | Coates | C23C 14/12 |
| | | | 427/2.24 |
| 2010/0163435 A1 | 7/2010 | Fischer | |
| 2011/0114744 A1 | 5/2011 | Ricciardi et al. | |
| 2013/0264226 A1 | 10/2013 | Prikril et al. | |
| 2018/0193537 A1 | 7/2018 | Honglei | |
| 2018/0272136 A1 | 9/2018 | Horn | |
| 2019/0125938 A1 | 5/2019 | Chen | |
| 2020/0345885 A1 | 11/2020 | Lewis | |

FOREIGN PATENT DOCUMENTS

| | | |
|---|---|---|
| CN | 101909666 A | 12/2010 |
| CN | 102026589 A | 4/2011 |
| CN | 102423266 A | 4/2012 |
| CN | 103083730 A | 5/2013 |
| CN | 203647752 U | 6/2014 |
| CN | 104203125 A | 12/2014 |
| CN | 106730044 A | 5/2017 |
| CN | 107454835 A | 12/2017 |
| EP | 0761243 A1 | 3/1997 |
| EP | 1510558 A1 | 3/2005 |
| EP | 2833799 A1 | 2/2015 |
| EP | 2833799 B1 | 8/2017 |
| WO | 1993/07924 A1 | 4/1993 |
| WO | 2004032704 A2 | 4/2004 |
| WO | 2004037443 A1 | 5/2004 |
| WO | 2009046093 A2 | 4/2009 |
| WO | 2017218832 A1 | 12/2017 |

OTHER PUBLICATIONS

International Search Report dated Feb. 27, 2020 for Application No. PCT/IB2019/060231.

International Search Report dated Feb. 27, 2020 for Application No. PCT/IB2019/060232.

* cited by examiner

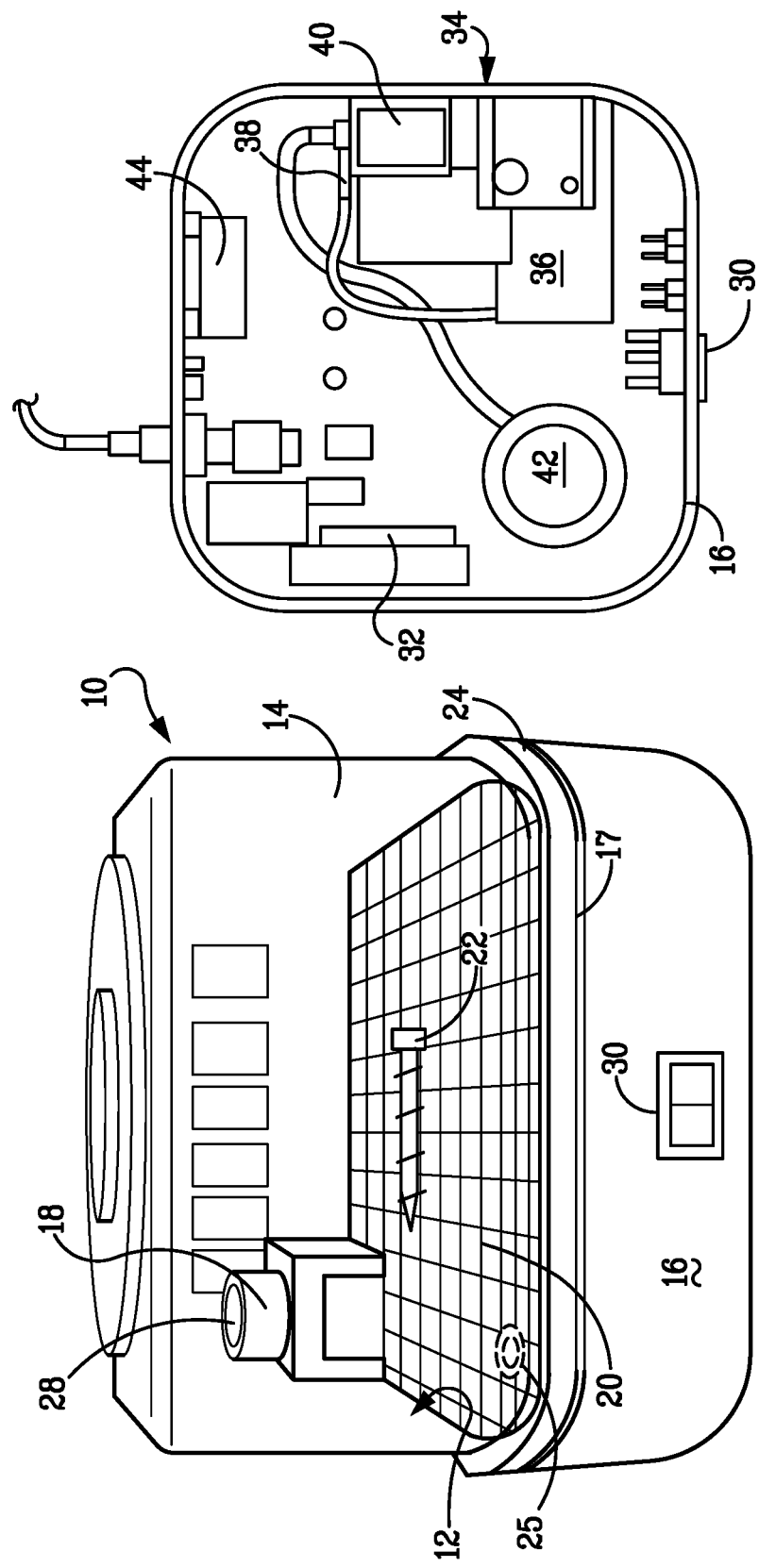

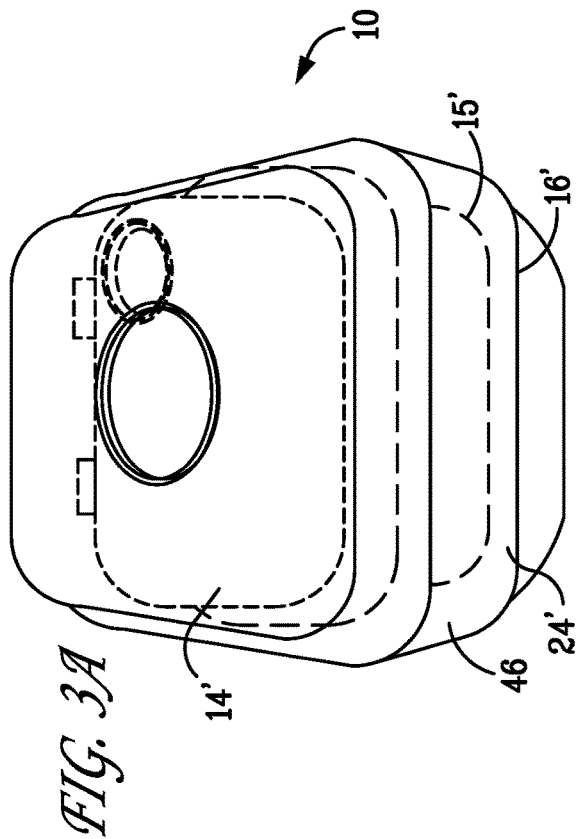
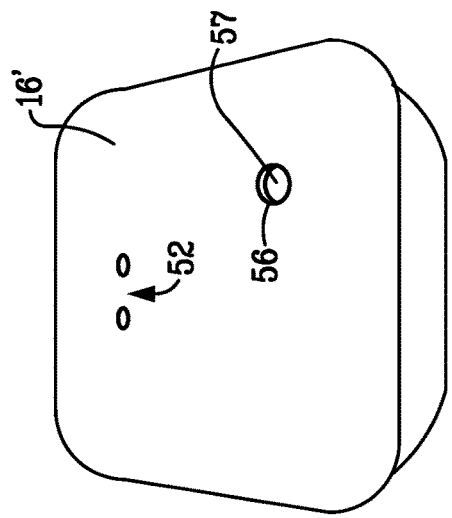
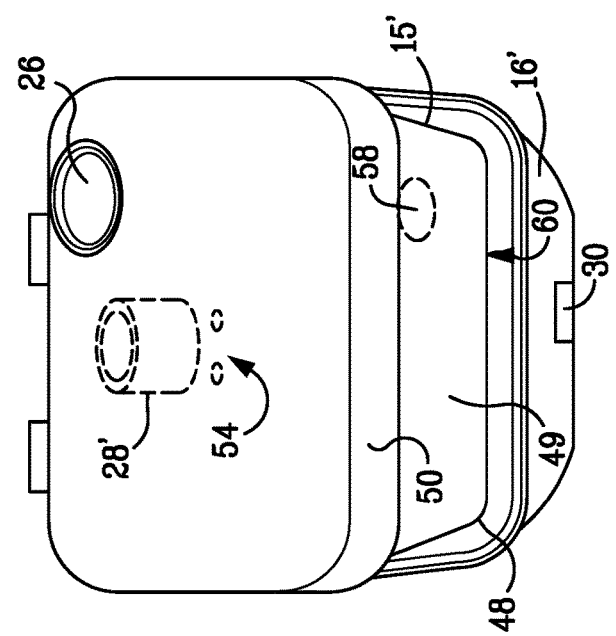
FIG. 3A
FIG. 3B
FIG. 3C

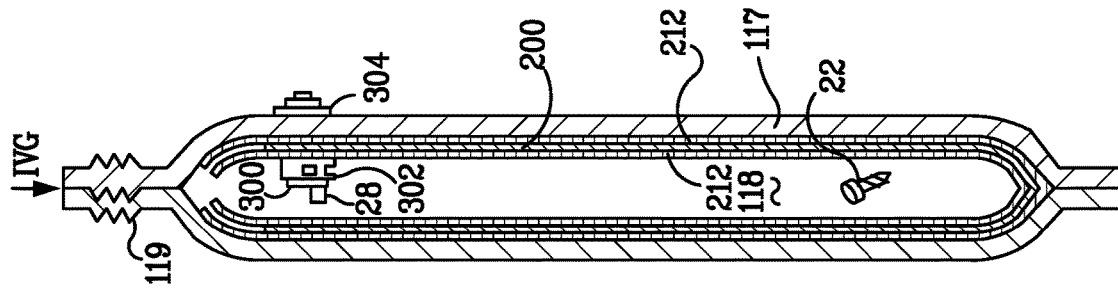
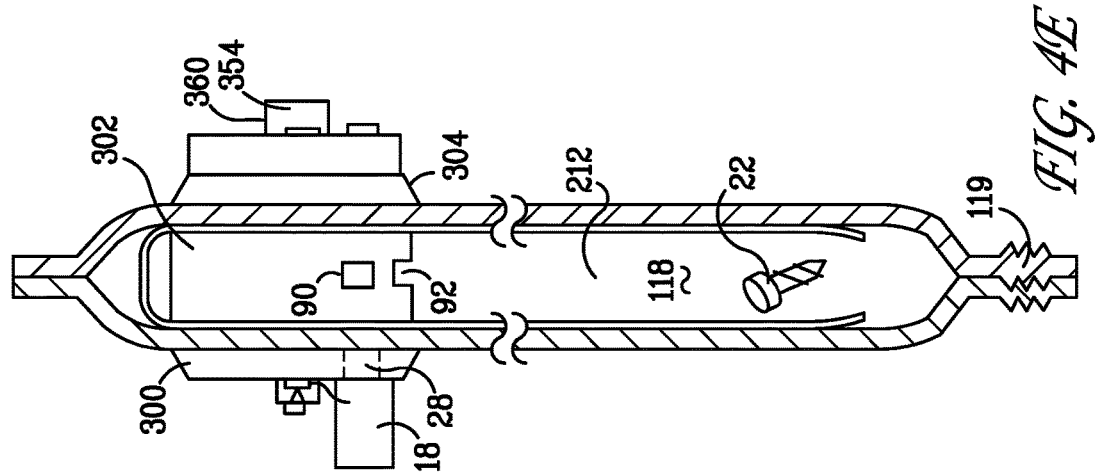
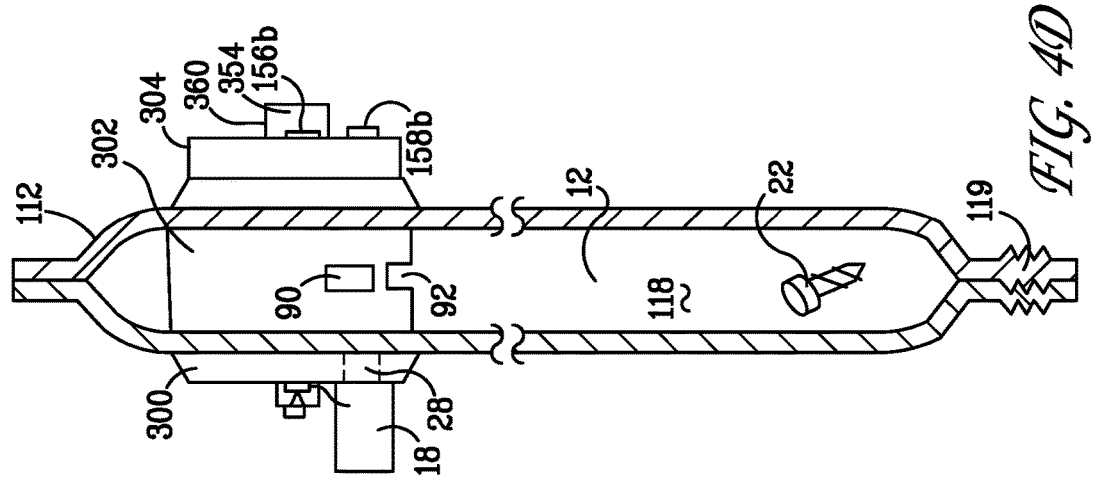

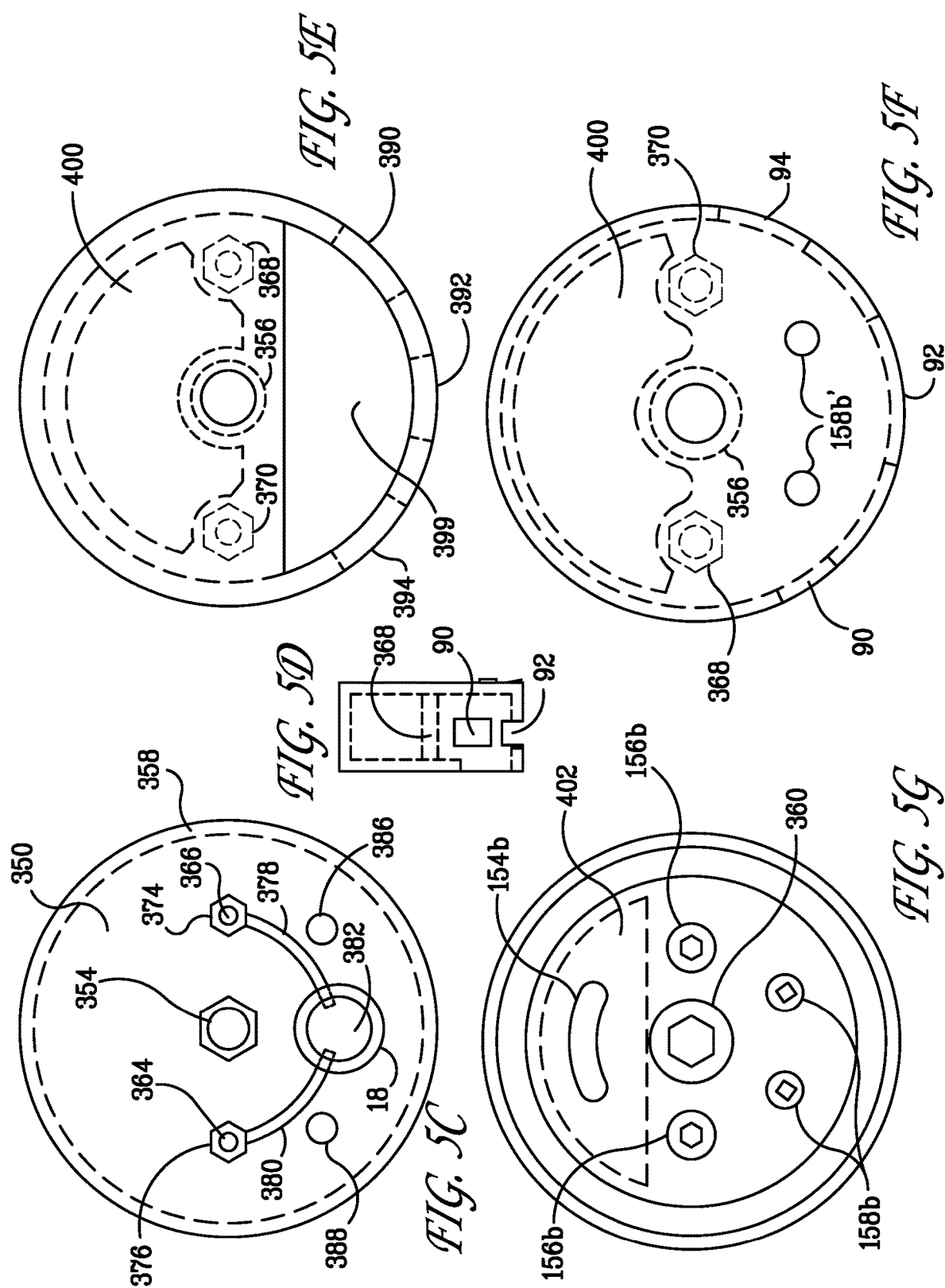

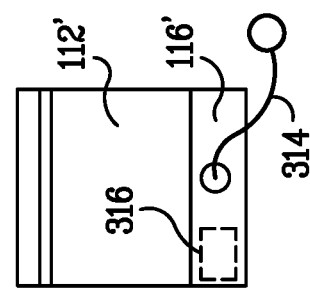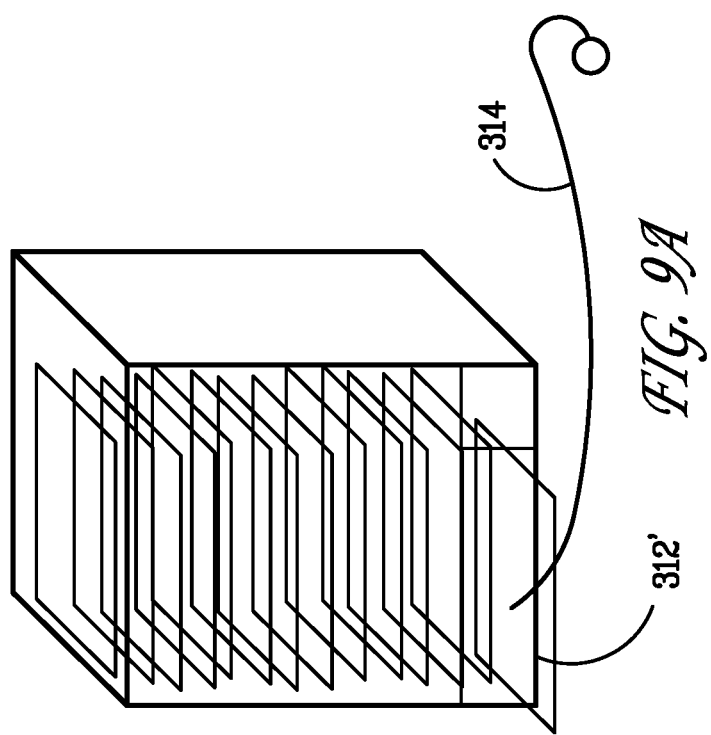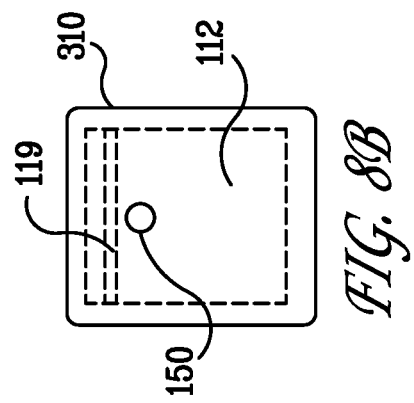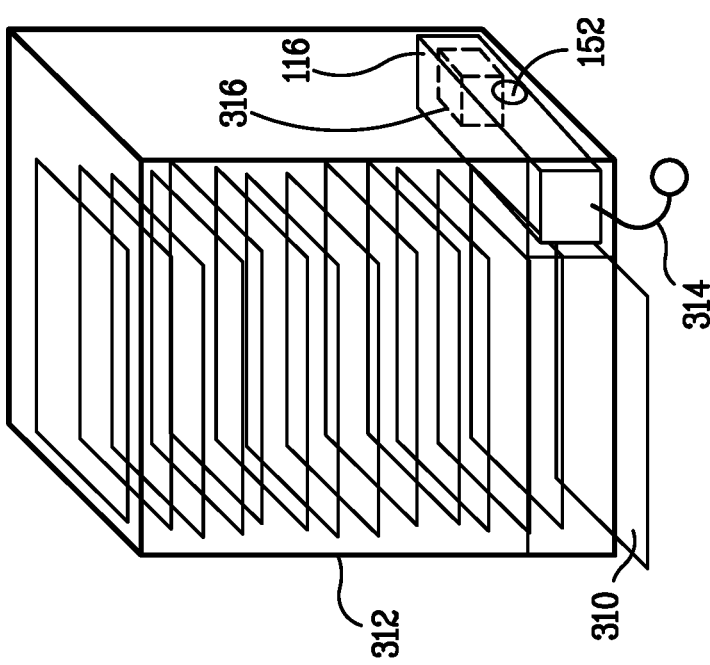
FIG. 8A
FIG. 8B
FIG. 9A
FIG. 9B

OPERATING ROOM COATING APPLICATOR AND METHOD

CROSS-REFERENCE TO RELATED APPLICATIONS

This application claims the benefit of U.S. Provisional Application No. 62/773,102 filed Nov. 29, 2018, the contents of which is incorporated herein by reference in its entirety for all purposes.

This application is related to U.S. Non-Provisional application Ser. No. 16/697,225, and to U.S. Non-Provisional application Ser. No. 16/697,228, being filed concurrently herewith and having common assignees.

FIELD

The present disclosure relates generally to apparatus and method for coating objects with a therapeutic agent, and more particularly, apparatus and methods suitable for use in an operating room to coat surgical instruments or surgical implants with a therapeutic agent in the course of conducting surgery, with minimal interruption and delay.

ENVIRONMENT

Each year, about twenty-seven million surgical procedures are performed in the United States, Post-operative or surgical site infections ("SSIs") occur in approximately two to three percent of all cases. This rate corresponds with the occurrence of more than 675,000 SSIs each year.

The occurrence of SSIs is often associated with bacteria that can colonize on implantable medical devices used in surgery. During a surgical procedure, bacteria from the surrounding atmosphere may enter the surgical site and attach to the medical device. Specifically, bacteria can spread by using the implanted medical device as a pathway to surrounding tissue. Such bacterial colonization on the medical device may lead to infection and trauma to the patient. Accordingly, SSIs may significantly increase the risks and costs of treatment to patients.

Implantable medical devices that contain antimicrobial agents applied to or incorporated within have been disclosed and/or exemplified in the art. Examples of such devices are disclosed in European Patent Application No. EP 0 761 243. Actual devices exemplified in the application include French Percuflex catheters. The catheters were dip-coated in a coating bath containing 2,4,4'-tricloro-2-hydroxydiphenyl ether (Ciba Geigy Irgasan (DP300)) and other additives. The catheters then were sterilized with ethylene oxide and stored for thirty days. Catheters coated with such solutions exhibited antimicrobial properties, i.e., they produced a zone of inhibition when placed in a growth medium and challenged with microorganism, for thirty days after being coated.

Most implantable medical devices are manufactured, sterilized and contained in packages until opened for use in a surgical procedure. During surgery, the opened package containing the medical device, packaging components contained therein, and the medical device, are exposed to the operating room atmosphere, where bacteria from the air may be introduced. Incorporating antimicrobial properties into the package and/or the packaging components contained therein substantially prevents bacterial colonization on the package and components once the package has been opened. The antimicrobial package and/or packaging components in combination with the incorporation of antimicrobial properties onto the medical device itself would substantially ensure an antimicrobial environment about the sterilized medical device.

US Published Patent Application 2004/0220614 of Scalzo, et. al., incorporated herein by reference in its entirety, describes an antimicrobial suture assembly comprising a containment compartment comprising one or more surfaces having an antimicrobial agent disposed thereon, said antimicrobial agent being selected from the group consisting of halogenated hydroxyl ethers, acyloxydiphenyl ethers, and combinations thereof, in an amount sufficient to substantially inhibit bacterial colonization on said containment compartment; and a suture positioned within the containment compartment, the suture comprising one or more surfaces having an antimicrobial agent disposed thereon, said antimicrobial agent being selected from the group consisting of halogenated hydroxyl ethers, acyloxydiphenyl ethers, and combinations thereof, and at least one active agent selected from the group consisting of a biocide, a disinfectant, an antiseptic, an antibiotic, an antimicrobial peptide, a lytic bacteriophage, a surfactant; an adhesion blocker; an oligonucleotide, an efflux pump inhibitors; a photosensitive dye, an immune modulator and a chelator.

SUMMARY

An aspect of the present disclosure provides a coating applicator operable to apply a coating of a therapeutic agent upon an object to be coated, comprising an openable and sealable device compartment, a therapeutic agent positioned in communication with the device compartment, an atomizer operable to atomize the therapeutic agent, and a source of vacuum in communication with the device compartment.

The object to be coated may be a surgical implant and/or a medical device.

In some embodiments, the coating applicator may further comprise a drier, and the drier may comprise an arrangement to operate the source of vacuum for a time sufficient to promote vacuum drying of the therapeutic agent and/or comprise an arrangement to apply heat in a region of the device compartment and/or comprise an arrangement to communicate heat released from a chemical reaction. In some embodiments the device compartment is openable and sealable with a vacuum lid.

In various embodiments, the therapeutic agent may be contained in a reservoir, wherein the reservoir may be fillable from a dispensing device.

In some embodiments, the atomizer may comprise a nebulizer and/or an ultrasonic nebulizer and/or a jet nebulizer and/or a vibrating mesh nebulizer and/or a pressurized spray nozzle nebulizer and/or a vibrated frit nebulizer and/or a thermally driven, wick-fed aerosol generator and/or a heated capillary aerosol generator and/or a vaporizer.

In some embodiments the therapeutic agent may comprise a liquid and/or an aqueous suspension and/or an emulsion and/or an aqueous solution.

In yet other embodiments, the device compartment may comprise a rigid wall, wherein the device compartment may comprise a vacuum lid, a base which may be configured to receive edge portions of the vacuum lid, and a seal which may be operative between the base and edge portions of the vacuum lid, and wherein the base may provide support for the source of vacuum and/or the atomizer and/or the object to be coated.

In still another embodiment, the coating applicator may further comprise a base comprising a first connection which may be operable to communicate the source of vacuum with the device compartment and a second connection which may be operable to communicate a source of electrical power to the device compartment for operating the atomizer, and a vacuum lid which may be removably and sealably connectable to the base, whereby a sealed space is established about the device compartment.

In various embodiments, the device compartment may comprise an openable box which may be configured for placement within the sealed space, wherein the openable box may comprise a support for the object to be coated, and/or a first receiver for receiving the first connection of the base, and/or a second receiver for receiving the second connection of the base. The atomizer may be disposed wholly within the openable box.

In some further embodiments, the device compartment may comprise a flexible wall and/or the device compartment may be openable and/or resealable along a first end portion. The vacuum source may be fluidly communicated with the device compartment at a location spaced from or adjacent the first end portion.

In some embodiments, the coating applicator may further comprise an accessory unit operable to communicate the source of vacuum with the device compartment, the accessory unit being further operable to connect a source of electrical power with the atomizer. In some embodiments, the atomizer may be disposed wholly within the device compartment and/or the coating applicator may further comprise a tether which may be operable to remotely connect the accessory unit with the device compartment, whereby the device compartment may remain in a sterile field of an operating room while the accessory unit may be operated at another location in the operating room.

In yet other embodiments, the accessory unit may be integrated with a single device chamber and in others, the coating applicator may further comprise a plurality of discrete device compartments, with the accessory unit being repetitively attachable with different members of the plurality of discrete device compartments. In some embodiments, the coating applicator may further comprise a tether which may be operable to remotely connect the accessory unit with an external source of vacuum and/or connect the accessory unit with an external source of electrical power, whereby the device compartment and the accessory unit may remain in a sterile field of an operating room during their operation.

In some embodiments, the flexible wall may comprise a flexible outer wall, a planar heating element, a planar first spacer which may be disposed between the flexible outer wall and the planar heater, and a planar second spacer which may be disposed between the planar heater and an interior of the device compartment. The first and/or the second planar spacers may comprise a mesh and/or the heater may comprise a serpentine heater.

Another aspect of the present disclosure provides a method of coating an object with a therapeutic agent comprising placing an object to be coated in a device compartment, sealing the device compartment, dispersing a therapeutic agent within the sealed device compartment by atomizing the therapeutic agent, whereby a coating of the therapeutic agent is established, drying the coating, and removing the coated object from the device compartment.

In some embodiments, the drying may comprise communicating a source of vacuum with the device compartment and/or the atomizing may comprise operating a nebulizer.

In some embodiments, the method may further comprise promoting deposition of the atomized therapeutic agent upon the object by: establishing the object in a chilled condition, and/or contacting the object with the atomized therapeutic agent while the object is in the chilled condition. The establishing may comprise cooling the object to below an ambient temperature, wherein the ambient may be in the range of approximately 20° C. to 25° C. In some embodiments, the establishing may comprise cooling the object to a temperature in the range of approximately −50° C. to approximately 15° C. The contacting may be continued for a time period in the range of approximately 1 to approximately 15 minutes or more. During the time period of contacting, the temperature of the object in the chilled condition may be increased by less than 15° C.

A further aspect of the present disclosure provides a method of depositing a therapeutic agent comprising cooling a surgical object to a temperature in the range of approximately −50° C. to approximately 15° C., nebulizing a therapeutic agent, and contacting the cooled surgical object with the nebulized therapeutic agent for a time period sufficient for the nebulized therapeutic agent to deposit upon a surface of the surgical object while the temperature of the surgical object remains below the ambient.

In some embodiments, the method may further comprise opening a device compartment, placing the surgical object in the device compartment, and closing the device compartment, communicating the nebulized therapeutic agent to the closed device compartment, evacuating the closed device compartment, and opening the device compartment and removing the surgical object.

In various embodiments, the method may further comprise drying the deposited therapeutic agent by communicating a source of vacuum with the closed object compartment and/or heating the atomized therapeutic agent to a heated condition and/or contacting the surgical object with the nebulized therapeutic agent while the nebulized therapeutic agent is in the heated condition. During the contacting, the temperature of the chilled surgical object may be increased by less than 15° C. such as by limiting the period of contacting.

BRIEF DESCRIPTION OF THE DRAWING

The embodiments shown in the figures of the accompanying drawing and subsequently described herein are presented by way of example, and not by way of limitation. In the figures, like reference numerals refer to similar elements; and wherein:

FIG. 1 is a perspective view of an operating room coating applicator constructed in accordance with an embodiment of the present disclosure;

FIG. 2 is a bottom planar view of a base portion of the operating room coating applicator shown in FIG. 1, with its bottom cover plate removed, in accordance with an embodiment of the present disclosure;

FIG. 3A is a perspective view of an operating room coating applicator constructed in accordance with another embodiment of the present disclosure;

FIG. 3B is a perspective view of the operating room coating applicator shown in FIG. 3A, but with the vacuum lid removed;

FIG. 3C is a perspective view of the base unit of the operating room coating applicator shown in FIG. 3A, wherein both the vacuum lid and the device compartment box have been removed from the base unit;

FIG. 4D is a cross-sectional side view of the device compartment bag shown in FIG. 4C, as viewed from the direction of the double arrow IVD-IVD in FIG. 4C, with FIG. 4D, in accordance with an example embodiment of the disclosure;

FIG. 4E is a cross-sectional side view of another embodiment of the device compartment bag shown in FIG. 4D which embodiment includes a spacer mesh within its device compartment thereof, in accordance with an example embodiment of the disclosure;

FIG. 4F is a cross-sectional side view of yet another embodiment of the device compartment bag shown in FIG. 4D which embodiment includes within its device compartment a first and second spacer mesh and a serpentine heater element disposed therebetween, in accordance with an example embodiment of the disclosure;

FIG. 5C is a planar end view of an inner end piece of the bag adapter element shown in FIG. 5B, as viewed in the direction of arrow VC in FIG. 5B, in accordance with an embodiment of the disclosure;

FIG. 5D is a planar side view of a middle piece of the bag adapter element shown in FIG. 5B, as viewed in the direction of arrow VD in FIG. 5B, in accordance with an embodiment of the disclosure;

FIG. 5E is a planar end view of the middle piece shown in FIG. 5B, as viewed in the direction of arrow VE in FIG. 5B and including a representation of an optional body of fibrous absorbent which may be contained within the middle piece, in accordance with an embodiment of the disclosure;

FIG. 5F is a planar end view of the middle piece shown in FIG. 5B, as viewed in the direction of arrow VF in FIG. 5B and including a representation of an optional body of fibrous absorbent which may be contained within the middle piece, in accordance with an embodiment of the disclosure;

FIG. 5G is a planar end view of the outer end piece of the bag adapter element shown in FIG. 5B, as viewed in the direction of arrow VG in FIG. 5B, in accordance with an embodiment of the disclosure;

FIGS. 7A-H are perspective views of an example embodiment of a method of coating an object using the operating room coating applicator shown in FIGS. 4H and 4G, wherein:

FIG. 7A shows an example of retrieving an accessory unit and a sealed packet containing a device compartment bag at a location that may lie outside a sterile zone of an operating room;

FIG. 7B shows an example of transferring a device compartment bag into the sterile field of an operating room and opening the packet;

FIG. 7C shows an example of inserting a surgical implant into an opened device compartment bag at a location which may lie within the sterile field;

FIG. 7D shows an example of resealing the device compartment bag while at the location within the sterile field;

FIG. 7E shows an example of transferring the re-sealed device compartment bag out of the sterile field of an operating room;

FIG. 7F shows an example of connecting the resealed device compartment bag an accessory unit at a location that may lie outside of the sterile field;

FIG. 7G shows an example of dispensing an amount of therapeutic agent into a reservoir of a nebulizer disposed outside the resealed device compartment bag while at the location which may be outside the sterile field and starting the accessory unit to execute a coating application cycle; and FIG. 7H shows an example of transferring a coated implant back into the sterile field of an operating room after completion of the coating application cycle and after returning the resealed device compartment bag to the location within the sterile field;

FIG. 8A is a perspective representation of an example of a dispenser being configured to dispense a plurality of sealed packets of device compartment bags and being configured to fixedly support an accessory unit thereon, in accordance with still another embodiment of the present disclosure;

FIG. 8B is a planar side view of an example of a sealed packet of the embodiment shown in FIG. 8A, the sealed packet comprising a contained device compartment bag and an outer primary packaging configured to ensure sterility of the contained device compartment bag;

FIG. 9A is a perspective representation of an example of another dispenser filled with sealed packets, each packet comprising coating applicator contained in an outer primary packaging, in accordance with yet another embodiment of the present disclosure;

FIG. 9B is a planar side view of an example coating applicator of a sealed packet as shown in FIG. 9A, with the outer primary packaging having been removed;

FIG. 10 is a graphical representation of a coating cycle for the application of a nebulized gentamicin mist to an implant, executable by various embodiments of the operating room coating applicator disclosed herein; and FIG. 11 is a photograph of a zone of inhibition test for gentamicin, described in the Example.

DETAILED DESCRIPTION

The medical and surgical devices referenced herein may include surgical instruments and implantable medical devices, wherein the latter may include but are not limited to orthopedic implants for trauma or joint reconstruction, breast implants, sternum closure devices, pacemakers, mono and multifilament sutures, surgical meshes such as hernia repair mesh, hernia plugs, brachy seed spacers, suture cups, suture anchors, adhesion prevention meshes and films, and suture knot clips. Implantable medical devices may be absorbable or non-absorbable.

Figure 4C:
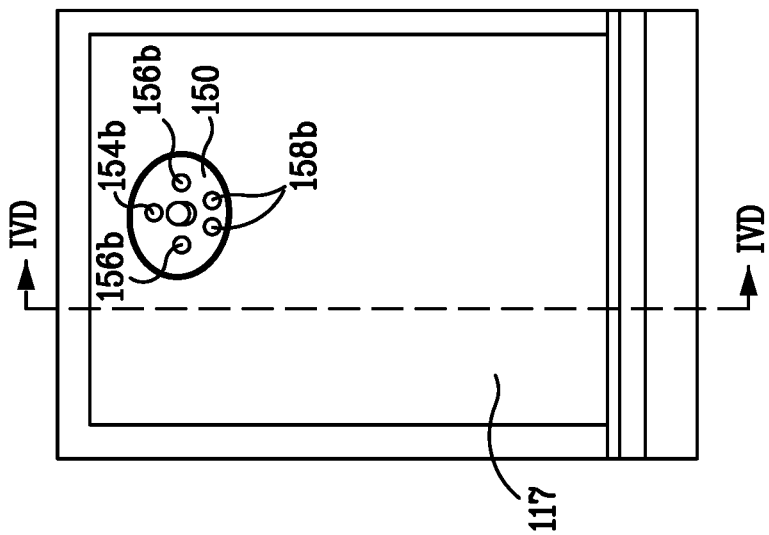
FIG. 4C is a planar side view of an accessory side of the device compartment bag shown in FIG. 4A, having been uncoupled from the accessory base unit shown in FIG. 4A.

An absorbable polymer, when exposed to physiological conditions, will degrade and be absorbed by the body over a period of time. Absorbable medical devices typically are formed from generally known, conventional absorbable polymers including, but not limited to, glycolide, lactide, co-polymers of glycolide, or mixtures of polymers, such as polydioxanone, polycaprolactone and equivalents thereof. Preferably, the polymers include polymeric materials selected from the group consisting of greater than about 70% polymerized glycolide, greater than about 70% polymerized lactide, polymerized 1,4-dioxan-2-one, greater than about 70% polypeptide, copolymers of glycolide and lactide, greater than about 70% cellulosics and cellulosic derivatives. Examples of absorbable medical device may include mono and multifilament sutures. The multifilament suture may include sutures wherein a plurality of filaments may be formed into a braided structure.

Examples of non-absorbable medical devices may include orthopedic implants for trauma or joint reconstruction, breast implants, sternum closure devices, pacemakers, mono and multifilament sutures, surgical meshes such as hernia repair mesh, hernia plugs and brachy seed spacers, which may be polymeric or nonpolymeric. Non-absorbable polymers include polyolefins, polyamides, polyesters, and polycarbonates and the like.

One particularly preferred antimicrobial agent is gentamicin. Gentamicin is a broad-spectrum antimicrobial agent that has been used in a variety of products, and is effective against a number of organisms commonly associated with SSIs. Such microorganisms include, but are not limited to, genus *Staphylococcus, Staphylococcus epidermidis, Staphylococcus aureus*, methicillin-resistant *Staphylococcus epidermidis*, methicillin-resistant *Staphylococcus aureus*, and combinations thereof.

During the manufacturing process medical devices may be coated with a composition comprising an antimicrobial agent. The coating may be applied to the device by, for example, dip coating, spray coating, suspended drop coating, or any other coating means. However, such techniques for establishing coatings on packaged surgical devices (implants and/or instruments) during or after their manufacture may present problems. For example, depending on the chemistry and other factors, some coatings may have a tendency to migrate over time from the coated device to its packaging, thereby reducing the amount of coating on the device itself. Again, depending on its chemistry and other factors, some coatings may degrade over time and therefore have a limited shelf-life. Robust sterilization processes that can compromise the integrity of the antimicrobial agent, such as gamma irradiation, e-beam irradiation, heat or steam, are often used in primary sterilization processes. Lastly, a coated, packaged device is subject to handling, which may inadvertently mechanically degrade some coatings. Furthermore, these techniques may have rather extended cycle times and may often require rather large machines to apply the coating, which are not conducive for operation in the limited space of an operating room, where time and space are limited.

Microorganisms of the genus *Staphylococcus* are the most prevalent of all of the organisms associated with device-related surgical site infection. *S. aureus* and *S. epidermidis* are commonly present on patients' skin and as such are introduced easily into wounds. The efficacy of a particular antimicrobial agent against a particular microorganism is measured by its minimum inhibitory concentration (MIC), which is defined as the minimum concentration of that antimicrobial agent that must be present in an otherwise suitable growth medium for that microorganism, in order to render the growth medium unsuitable for that microorganism, i.e., the minimum concentration to inhibit growth of that microorganism. The phrase "an amount sufficient to substantially inhibit bacterial colonization" as used herein is defined as the minimum inhibitory concentration for *S. aureus* or greater.

A demonstration of this MIC is seen in the disk diffusion method of susceptibility. A filter paper disk, or other object, impregnated with a particular antimicrobial agent is applied to an agar medium that is inoculated with the test organism. Where the anti-microbial agent diffuses through the medium, and as long as the concentration of the antimicrobial agent is above the MIC, none of the susceptible organism will grow on or around the disk for some distance. This distance is called a zone of inhibition. Assuming the antimicrobial agent has a diffusion rate in the medium, the presence of a zone of inhibition around a disk impregnated with an antimicrobial agent indicates that the organism is inhibited by the presence of the antimicrobial agent in the otherwise satisfactory growth medium. The diameter of the zone of inhibition is inversely proportional to the MIC.

Referring now to FIG. 1 in accordance with an example embodiment, the present disclosure provides an operating room coating applicator 10 comprising a device compartment 12 which may be defined at least in part by the space enclosed when a vacuum lid 14 is engaged in a superposing relation with a base unit ("base") 16. In this and various other embodiments, a nebulizer or atomizer 28 may include a reservoir 18 and may be supported from the base 16 at the bottom of reservoir 18, such that the output of the nebulizer 28 is communicated to the device compartment 12. Upon operation of the nebulizer 28, a selected therapeutic agent, which is loaded into reservoir 18, may be atomized to produce an aerosol, mist, vapor, fog or cloud of the therapeutic agent within the confines of the device compartment 12.

The base 16 may be sized to accommodate the limited space is that may be available in an operating room. Space within the sterile field of an operating room may be even more limited. In the present example embodiment, the base 16 may have a footprint of a six-inch square or less.

The base 16 may house a device supporting platform 20, such as a grate or screen, in a region of the device compartment 12 for receiving an object to be coated 22. In various embodiments, the object 22 may comprise one or more surgical implants and/or surgical instruments and/or other articles useful in conducting oral surgery. In this embodiment, the device supporting platform 20 is in the form of a lattice grid-work which facilitates circulation of fluid above and below and through the platform 20 and promotes a more complete exposure of the surfaces of the object to be coated 22 to the aforementioned aerosol, mist, vapor, fog or cloud of therapeutic agent that may be produced in the device compartment 12. The vacuum lid 14 may be readily raised and lowered with respect to the base 16 so as to facilitate placement of the object to be coated 22 on the device supporting platform 20. A resilient O-ring 24 may be provided between edge portions 17 of the vacuum lid 14 and opposing portions of the base to effect a seal between the vacuum lid 14 and the base unit 16. It is envisioned that other suitable arrangements for effecting a seal between the lid 14 and the base 16 might be employed in lieu of or in conjunction with the O-ring seal 24.

In this embodiment, the base unit 16 may house and provide support for a source of vacuum, which may be communicated to the device compartment 12 through a vacuum port 25, (depicted in dashed lines in FIG. 1, because it is disposed beneath the platform 20 in this illustration). Upon communication of vacuum to the device compartment 12 through the vacuum port 25, the device compartment 12 may be evacuated of any lingering aerosol, mist, vapor or cloud of therapeutic agent. In this and other embodiments, the drawing action communicated to the device compartment 12 may be continued for a time sufficient to promote drying of any therapeutic agent deposited (coated) upon the object 22 resulting from its contact with the aforementioned aerosol, mist, vapor, fog or cloud of therapeutic agent. In various embodiments, the vacuum may be applied for a time sufficient to achieve a desired, reduced moisture level in the dried layer of therapeutic agent in the range of approximately 10 percent to 0 percent.

Upon completion of an application cycle, the coated surgical object 22 is removed from the confines of the device compartment 12 in a condition acceptable for immediate use in a surgical procedure being conducted within the sterile field of an operating room or the like. In various embodiments, the coating of the therapeutic agent upon the surgical object 22 is may or may not be microscopically uniform. The coating may be in the form of discrete microscopic islands dispersed across the surfaces of the implant or may have a thickness in the range of approximately 0.1 to 5 micrometer. In various embodiments, the gentamicin coating may be vacuum dried to a moisture content in the range of about 0 percent by weight of the coating.

In this embodiment and others, the nebulizer 28 may include and/or cooperate with a reservoir 18 configured to receive quanta of therapeutic agent that may be contemplated for the application. In this and various other embodiments, the therapeutic agent may be in the form of an aqueous solution and/or an aqueous suspension of the therapeutic agent. In various embodiments, the reservoir 18 may be open ended and/or in the form of a vial and therefore fillable with a dispenser such as a syringe or an eyedropper or other suitable dispenser. It is also envisioned, that the reservoir 18 may be prefilled and provided with a breachable cover whereby the therapeutic agent may be retained in the reservoir 18 until use.

The nebulizer 28 at the bottom of reservoir 18 may be in the form of a commonplace ultrasonic nebulizer, such as a vibrating piezoelectric disk, widely commercially available from suppliers worldwide such as AMAZON, including those which include regions of microscopic pores. It is envisioned that a number of different forms of atomizers may be used, such as by way of non-limiting examples, a jet nebulizer and/or a vibrating mesh nebulizer and/or a pressurized spray-nozzle nebulizer and/or a heated frit nebulizer and/or a heated wick aerosol generator and/or a heated capillary, among others. One common aspect that may be shared amongst devices being considered for use as an atomizer in accordance with this disclosure is a capability of the candidate atomizer to transform a solution or suspension of a therapeutic agent into mist, cloud vapor or aerosol comprising tiny liquid particles (tiny droplets) of a therapeutic agent that may remain suspended in air for a time sufficient to coat an object 22 in accordance with the teachings herein.

In various embodiments, the base 16 may be provided with a selector switch 30 for switching from one program of operation to another (such as amongst programs which provide differing drying cycles or soak times or the like) and/or for switching from one mode of operation to another and/or simply to turn on and off the operating room coating applicator 10.

Referring now also to FIG. 2, in this embodiment and various others, the base unit 16 may internally house and provide support for a controller 32 which may be in the form of a micro-processor or other suitable electronic arrangement for controlling the timing of a coating cycle, the communication of vacuum with the device compartment 12, operation of the nebulizer 28, and in some other embodiments, the application of heat within the device compartment 12. In the present embodiment and various others, the controller 32 may be configured to execute a coating cycle such as the example coating cycle described with reference to FIG. 10 herein. Upon receipt of a signal to initiate the coating cycle, the controller 32 may turn on and provide electrical power to the nebulizer for a prescribed period of time or until a detected level of therapeutic agent has been atomized and/or until a level of liquid (un-atomized) therapeutic agent in the reservoir 18 has been detected. It is envisioned that other detectable factors may be communicated to the controller 32 for purposes of managing the time period for operation of the nebulizer 28. The controller 32 may also be configured to draw vacuum from the device compartment 12 for a prescribed period of time and/or upon achievement of a particular prescribed condition within the device compartment 12 and/or according to a program of repeated applications of vacuum, each with a common cycle time and or differing cycle times.

The base unit 16 may further provide support for a vacuum system 34 for communicating a source of vacuum to the device compartment 12, which may comprise a vacuum pump 36 and a conduit 38 for communicating the drawing action of the vacuum pump 36 to the device compartment 12. The vacuum system 34 may further comprise one or more solenoid valves 40 or other suitable valve to open and close the conduit 38 under the direction of the controller 32. During an evacuation of the device compartment 12, the air and other constituents (suspended, atomized therapeutic agent(s) and possibly other suspensions) that are withdrawn from the device compartment 12 may be directed through a vapor trap 42, whereby the suspension droplets may be collected. To release vacuum, the solenoid valve 40 may be tripped to allow air to reenter the device compartment 12. Operation of the various components of the vacuum system 34 may be controlled by the controller 32 to repetitively execute a prescribed operational cycle. For example, the controller 32 may be configured to operate the vacuum pump 36 and to communicate the drawing action of the vacuum pump 36 to the device compartment 12 for a predetermined period of time to effect a drying action upon any coating established on the object to be coated 22. It is to be understood that during such operation, the drawing action of the vacuum pump 36 may evacuate the device compartment 12 so that upon opening of the device compartment 12 after execution of the cycle, little or no residual therapeutic agent is allowed to escape from the device compartment 12 into the surrounding environment.

In this and other embodiments, the base unit 16 may also provide support for the nebulizer 28, including its ultrasonic signal driver 44. In various embodiments, the controller 32 may be configured to operate nebulizer 28 for a prescribed time or portion of an application cycle, such as for the first 30 seconds of a 220 second cycle. In some embodiments, the controller 32 may be configured to turn on the vacuum pump 36 upon conclusion of the operation of the nebulizer 28. In other embodiments, operation of the vacuum pump 36 may be delayed after operation of the nebulizer 28 has ceased so as to provide a soaking period within the application cycle. Of course, it is to be understood that the layout and sequence of an application cycle may vary depending on the nature of the object to be coated 22, the therapeutic agent to be applied, the efficiency of the vacuum pump 36 and/or efficiency of the nebulizer 28, among other factors.

Referring now to FIGS. 3A and 3B, in an example of another embodiment, an operating room coating applicator 10 may comprise an openable box-like device compartment 15', which may be configured to fit and lie within a space 46 enclosed by a removable, outer vacuum lid 14' and a base unit 16'. In this embodiment, the box-like device compartment 15' may comprise a lower box body 48 to which is hinged a box body top 50. In various other embodiments, the box body top 50 may be wholly removable from the box body 48 and/or threadably connected with the box body 48. As such, the device compartment 15' may be moved about independently of the base 16' such that the base 16' may be located outside a sterile zone of an operating room and the device compartment 15' may be separately utilized within the sterile zone.

The device compartment 15' may be provided with a vent 26' so as to allow equalization of pressure within the device compartment 15' and the space 46 defined between the vacuum lid 14' and the base 16'. In some embodiments, as the device compartment 15' is evacuated, the space 46 will also be evacuated via the vent 26'. The vent 26' may be constructed of a Tyvek® material and functions to allow pressure within the device compartment 15' to be equalized to the space 46 outside the device compartment 15' and under the vacuum lid 14'. With the use of Tyvek® material or other suitable material of comparable functionality, the atomized therapeutic agent may be substantially, if not entirely prevented from entering the space 46 outside the device compartment 15' and instead, may remain within the device compartment 15' until it is evacuated by an operation of the vacuum system 34.

It is noted that in this embodiment, the O-ring 24' provides a vacuum tight seal between the vacuum lid 14' and the base 16'.

In the present embodiment, the walls 49, 51 of the box body 48 and the lid of the box body 50, respectively, may be sufficiently rigid to withstand handling. However, because of the capacity of the vent 26' to equalize pressure on opposite sides of the walls 49, 51, the walls 49, 51 need not withstand the forces that would otherwise be induced by an operation of the vacuum system 34. Accordingly, the walls 49, 51 may be constructed from a thin plastic or other suitable material so as to minimize material waste upon their disposal.

In this and various other embodiments, the operative portion of the nebulizer 28' may be wholly disposed within the device compartment 15'.

Referring now also to FIG. 3C, the base unit 16' may be constructed in accordance with the teachings above in reference to the base 16 that is shown in FIGS. 1 and 2, except that the operative portion of the nebulizer 28' may be located in the box-like device compartment 15' instead of the base 16', in which case the base 16' may be provided with a first (electrical) connection 52 for communicating electrical power to the nebulizer 28' and to any other electrical device(s) disposed within in the box-like device compartment 15'. Likewise, the device compartment 15' may be provided with a complementary first receiver 54 (FIG. 3B), which electrically connects with the electric contacts of the first electrical connection 52 of the base 16'. In some embodiments, the first electrical connection 52 and/or the receiver 54 may include pins (which may be spring-loaded) or other suitable, releasable, electrical connectors.

The base unit 16' may also be provided with a second (vacuum) connection 56, which may comprise a vacuum port 57 configured to sealingly engage a corresponding vacuum port 58 located at an underside portion 60 of the device compartment 15'. The vacuum port 57 may be provided with O-rings or other suitable seal to establish a vacuum seal at the vacuum connection 56, whereby the vacuum pump 36 of the base 16' may be communicated with the interior of the device compartment 15'. However, the O-rings may be omitted, because of the vacuum seal established by the O-ring 24 between the vacuum lid 14 and the base unit 16.

In some embodiments, the device compartment 15' may be disposable; and both the device compartment 15' and the base 16' may be provided with magnetic pieces that are mutually disposed to assure proper alignment and easy connection of the electrical contacts 52 and 54 when the device compartment 15' and the base 16' are brought together.

Any of the above described embodiments and variations thereof may be utilized to coat an object 22 with a therapeutic agent where the agent which may be suitable for use with the nebulizer. The steps to coat the object with this type of therapeutic agent include:

opening the device compartment 15;

placing an object to be coated 22 upon the device support platform 20;

placing a small quantity of the therapeutic agent, such as a 5% aqueous solution of gentamicin into the reservoir 27 of the nebulizer 28;

closing the respective lid (14, 50) of the device compartment 15;

sealing the vacuum lid 14 to the base 16;

nebulizing the therapeutic agent for about 30 seconds to form a "fog" of the therapeutic agent within the device compartment 15;

drawing a vacuum inside the device compartment 15 for approximately 2 to 3 minutes to evacuate the interior of the device compartment 15 and to dry the coating of therapeutic agent;

releasing the vacuum;

removing the vacuum lid from the base 16;

opening the device compartment 15; and removing the coated object.

Referring now to FIGS. 4A-D, an example of an operating room coating applicator 10 constructed in accordance with another embodiment of the present disclosure comprises a device compartment bag 112 and an accessory base unit ("accessory") 116, the latter having many of the functionalities of the base units 16, 16' described in reference to the previously disclosed embodiments, including a controller 32'. In contrast to the rigid (or semi-rigid walls) of the device compartments 15, 15' of the previous embodiments, the walls 117 of the device compartment bag 112 may be flexible and may be opened along a ribbed closure 119 to accommodate placement of the object to be coated 22 within the confines (interior) 118 of the device compartment bag 112. The interior 118 of the device compartment bag 112 functions as a device compartment. The interior 118 the device compartment bag 112 may also accommodate certain components of the applicator 10 such as a middle piece 302 of an adapter 150 as shown in FIG. 4D and/or the nebulizer 28 including the reservoir 18 associated therewith as shown in FIG. 4F The device compartment bag 112 may also be provided with an adapter ("connector") 150 which is configured to releasably connect with a second corresponding adapter ("connector") 152 which may be provided upon the accessory 116. Engagement of the adapter 150 with the adapter 152 may be achieved with a sliding fit therebetween or a claw or detent engagement or a magnetic attachment or other suitable releasable arrangement. In various embodiments, the head 360 of a magnetic bolt 354 of the adapter 150 registers with and magnetically couples with a recessed element 153 of the adapter 152 of the accessory 116.

The adapters 150, 152 may be provided with corresponding ports 154a, 154b for establishing communication between a source of vacuum 136 of the accessory 116 and the interior 118 of device compartment bag 112. In various embodiments, an O-ring 157 about the recessed perimeter of the adapter 152 of the accessory 116 establishes a seal against the outer periphery 159 of the adapter 150 of the device compartment bag 112.

The adapters 150,152 may also be provided with corresponding pairs of electrical connectors 156a, 156b which may comprise spring-loaded, metallic pins or other suitable, releasable, electrical connection devices. Additional electrical connections may be established on the adapters 150, 152 at their respective locations 158a, 158b to connect other devices with the source of power 133 of the accessory 116. In various embodiments, the source of power 133 may comprise a battery or a pack of batteries 133 disposed within the accessory 116 or may instead or in addition comprise an electrical cord 133' for connection with an external electrical wall socket or an external battery or the like.

Alternatively, the adapter 152 of the accessory 116 may include spring-loaded pins at its location 158a which may serve as probes for temperature measurement and/or for pressure measurement and/or for transmitting an ultrasonic signal to the nebulizer 28. These pins could be extendable through ports established at the corresponding locations 158b of the adapter 150 of the device compartment bag 112.

Figure 4A:
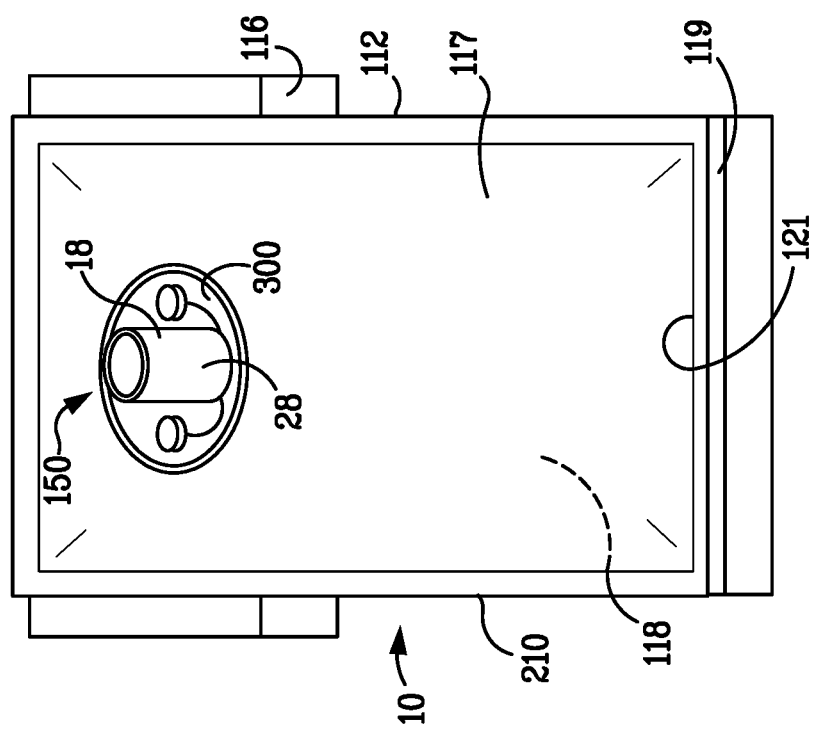
FIG. 4A is a perspective view of an operating room coating applicator constructed in accordance with another embodiment of the disclosure, which may comprise a device compartment bag which cooperates with an accessory base unit.
Figure 4H:
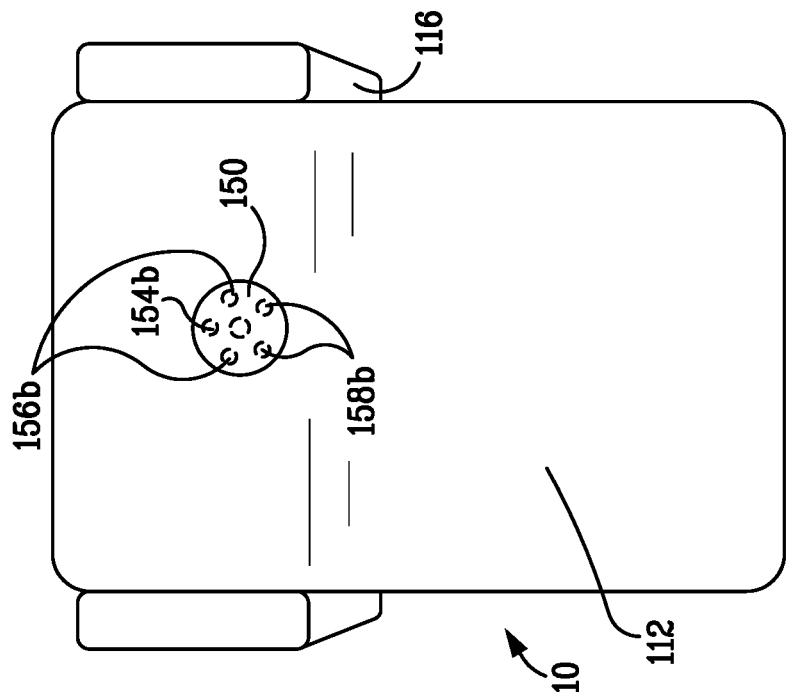
FIG. 4H is a perspective view of an operating room coating applicator comprising the device compartment bag shown in FIG. 4F and an accessory base unit, in accordance with an embodiment of the disclosure.
Figure 4B:
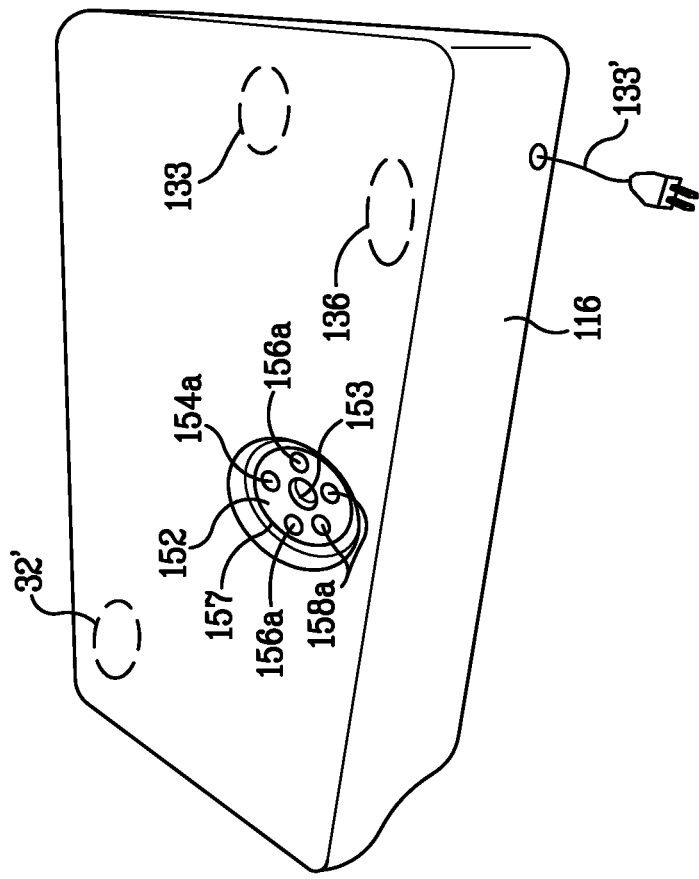
FIG. 4B is a perspective view of the accessory base unit shown in FIG. 4A, having been uncoupled from the device chamber bag shown in FIG. 4A.

Xxx move it is to be understood that in FIG. 4H, the adapter 150 of the device compartment bag 112 is hidden from view and therefore represented by dashed lines. In this embodiment, the ribbed seal 119 is located at the bottom portion 121 of the device compartment bag 112.

Referring now in particular to FIG. 4D, the adapter 150 of the device compartment bag 112 may be fixed to the device compartment bag 112 at a location spaced from a lower sealed end portion 123 of the device compartment bag 112, although the location of the adapter 150 may be other than that which is specifically shown and described. The adapter 150 may support the nebulizer 28 and its reservoir 18 with a first end piece 300 disposed outside of the device compartment bag 112 such that a desired quantity of therapeutic agent may be dispensed into the reservoir 18. Electrical power is communicated to the nebulizer 28 from the source of electrical power 133 of the accessory unit 116 via the electrical connection established at the interface between the connectors 156a and 156b of the adapters 152 and 150 of the accessory unit 116 and the device compartment bag 112, respectively.

The adapters 152, 150 may be provided with additional electrical connectors, such as electrical connectors 158a, 158b, respectively, to provide electrical connection for additional devices such as a resistive heater 200 (FIG. 6B) and/or a thermistor and/or other device. Additional sets of connectors may be established with the adapters 150, 152 depending on need.

Referring back to FIGS. 4A and 4C, the device compartment bag 112 may be formed by folding a flexible wall 117 and sealing the outer perimeter 210 along three sides of the folded wall 117. A resealable ribbed seal 119 may be established across the remaining end portion of the device compartment bag 112. In some embodiments, the adapter 150 of the device compartment bag 112 be located adjacent the ribbed seal 119 such as shown in FIG. 4F, and in other embodiments, the adapter 150 may be located in a spaced relation to the resealable ribbed seal 119 such as shown in FIGS. 4A and 4C, wherein the ribbed seal 119 may be established at the bottom portion 121 of the device compartment bag 112.

Figure 5A:
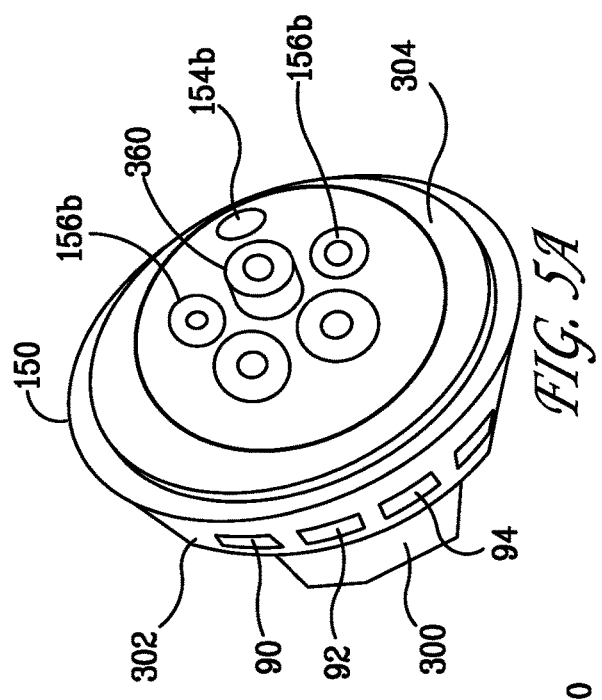
FIG. 5A is a detailed perspective view of the bag adapter element shown in FIGS. 4D-F, in accordance with an embodiment of the disclosure.
Figure 4G:
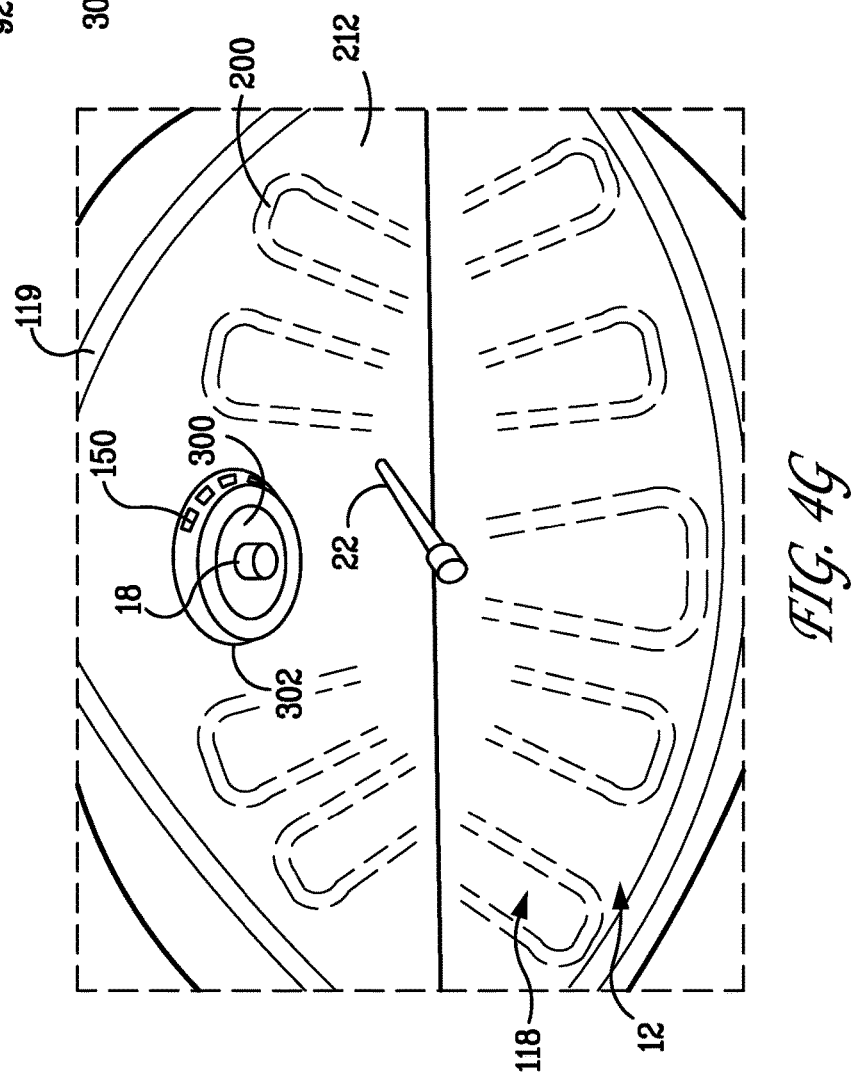
FIG. 4G is a top view in the direction of arrow IVG in FIG. 4F of the device compartment bag shown in FIG. 4F, with the bag having been opened, in accordance with an embodiment of the present disclosure.
Figure 5B:
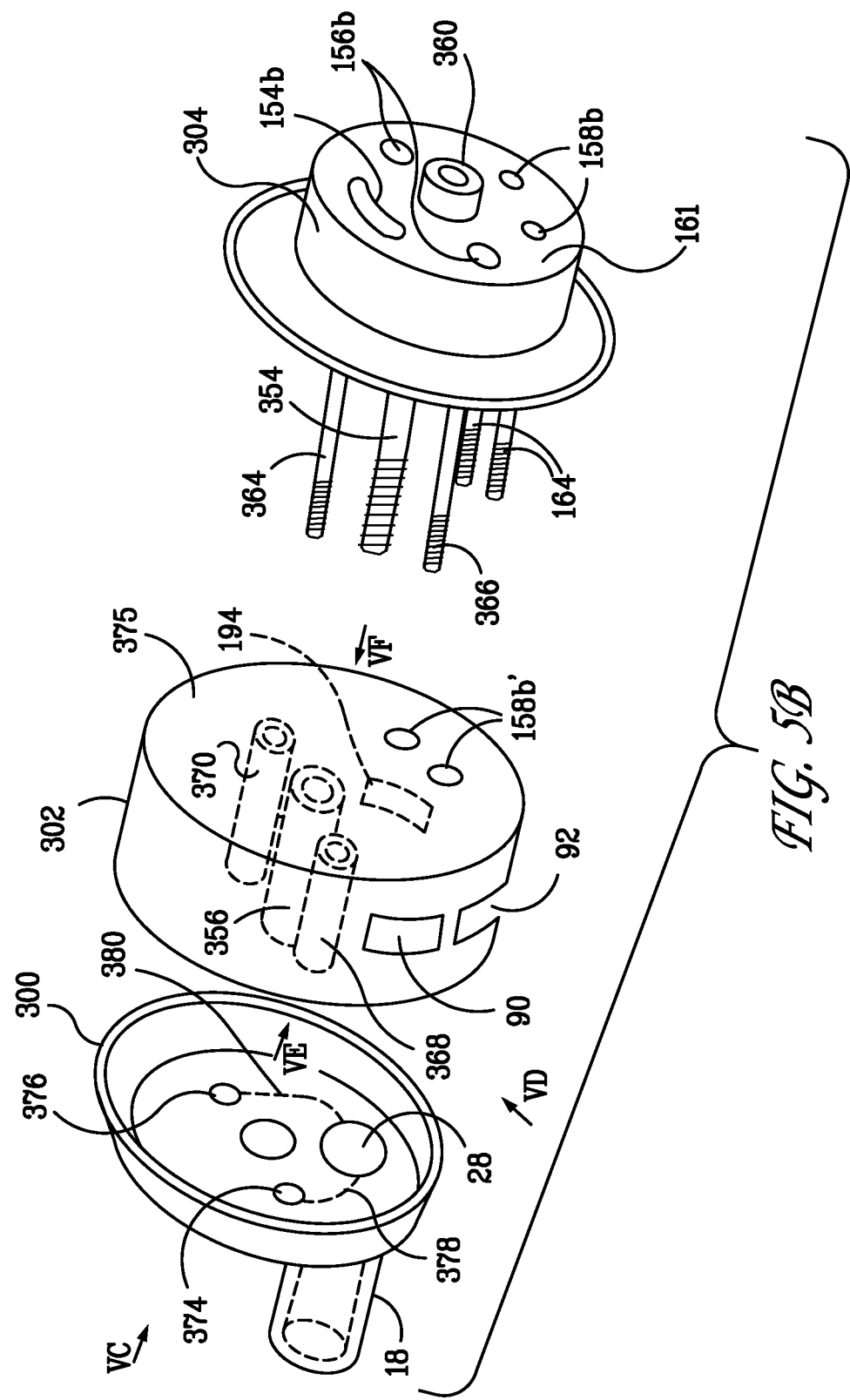
FIG. 5B is an exploded perspective view of the bag adapter element shown in FIG. 5A, in accordance with an embodiment of the disclosure.

Referring now to FIGS. 5A and 5B, in an embodiment, the adapter 150 of the compartment bag 112 may comprise an first end piece 300 which may provide rigid support for the nebulizer 28 and its reservoir 18, a central piece 302 which may provide ports 390, 392, 394 for communicating both the drawing of vacuum from a source of vacuum 136 (of the accessory 116) and the output of the nebulizer 28 to the interior 118 of the device compartment bag 112 and an second end piece 304 which may be configured to provide the vacuum port 154b, support for the electrical connectors 156b and 158b, and/or provide a releasable connection with the adapter 152 of the accessory unit 116 which in the present embodiment may comprise the magnetic bolt head 360.

Referring to FIGS. 5C and 5E, in various embodiments, the nebulizer 28 may be supported from a side 350 of the first end piece 300 such that its output may be communicated directly into an offset open space 399 of the middle piece 302. The nebulizer 128 may be offset from a smooth or threaded bore 352 located centrally on the first end piece 300 for receiving an end portion of a central, tightening bolt 354. The central bolt 354 may extend from a central portion of the second end piece 304 through a central, tube like via 356 of the middle piece 302 and into the bore 352 of the first end piece 300. In various embodiments the central bolt 354 is tightened by threading it into the central bore 352 of the first end piece 300 and/or threading it into a nut 353 such that the three pieces 300, 302, 304 are mutually sealed and secured to one another. To further assure sealing, an O-ring 358 may be disposed between the first end piece 300 and the middle piece 302 and a second O-ring 359 may be disposed between the middle piece 302 and the second end piece 304. In various embodiments, an undersized cut out may be established in the flexible wall 117 on both sides of the bag 116 at the desired location for the adapter 150, leaving sufficient material which may be sealingly clamped between the first end piece 300, the middle piece 302 and the second end piece 304.

In lieu or in addition to the O-ring seals 358, 359, ultrasonic and/or RF welding techniques may be used to mate the pieces 300, 302, 304 and to seal portions of the bag 112 thereto.

In various embodiments, the central bolt 354 may be magnetized to help retain the device compartment bag 116 once placed and connected with the accessory unit 116. Additionally, the head of the bolt 360 may protrude beyond the outer plane 161 of the second end piece 304 such that during use of the operating room coating applicator 10, it may be inserted into and registered with a corresponding central recess 153 provided in the adapter 152 of the accessory unit 116 (FIG. 4B).

Referring to FIGS. 5B, 5E and 5F, the adapter 150 of the device compartment bag 112 may include additional pins 364, 366 which may extend from the plane 161 of the second end piece 304, through tubular guides (vias) 368 and 370 provided in the central piece 302 and into electrical receivers 374, 376 of the first end piece 300. In various embodiments, the pins 364, 366 may be provided with threaded ends which may be threaded into the receivers 374, 376 of the end piece 300. The end piece 300 may further include printed and/or wired electric leads 378, 380 leading from the receivers 374, 376 to the transducer 382 of the nebulizer 28. The receivers 374, 376 may comprise electrically conductive nuts. The printed and/or wired electric leads 378, 380 may be disposed along the side 350 of the end piece 300 (or on its opposite side which faces the middle piece 302). In effect, the heads of the pins 364, 366 may serve as the previously described connectors 156*b* of the adapter 150. By such arrangements, an electrical connection may be established to the nebulizer 28 via the pins 364, 366.

The tubular guides (vias) 368 and 370 of the middle piece 300 extend from the fully closed face 375 of the piece 300, which positions adjacent the second end piece 304, and a partial, crescent shaped face 377 at the opposite end of the middle piece 302, which positions adjacent the first end piece 300. Referring specifically to FIG. 5E, partial crescent shaped face 377 presents the opening 399 for admission of the output of the nebulizer 28 into the centerpiece 302.

In some embodiments, a second set of pins 164 (shown in FIG. 5B) may be extended through the second end piece 304 and through tubular guides (vias) 369, 371 of the middle piece 302, and to the first end piece 300 whereupon they may be connected to receivers 386, 388 of the first end piece 300. Such arrangement may be used to establish additional electrical connection for additional electrical devices to be located at the first end piece 300, such as a heater, a sensor or a thermistor or other device, if desired.

Figure 6A:
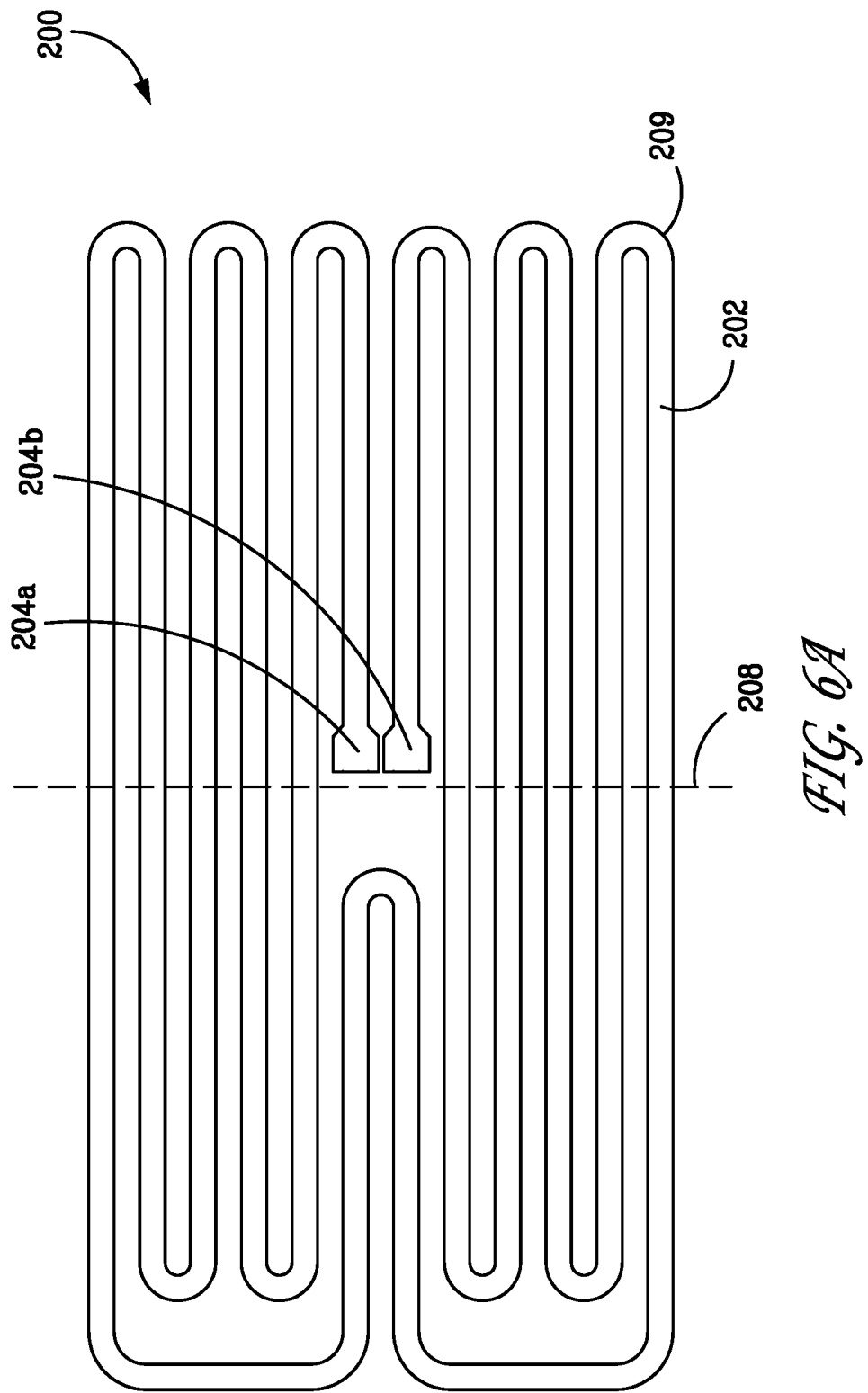
FIG. 6A is a side planar view of a possible pattern of an electrically resistive heater element prior to its being folded and inserted into a device compartment bag, in accordance with an embodiment of the disclosure.
Figure 6B:
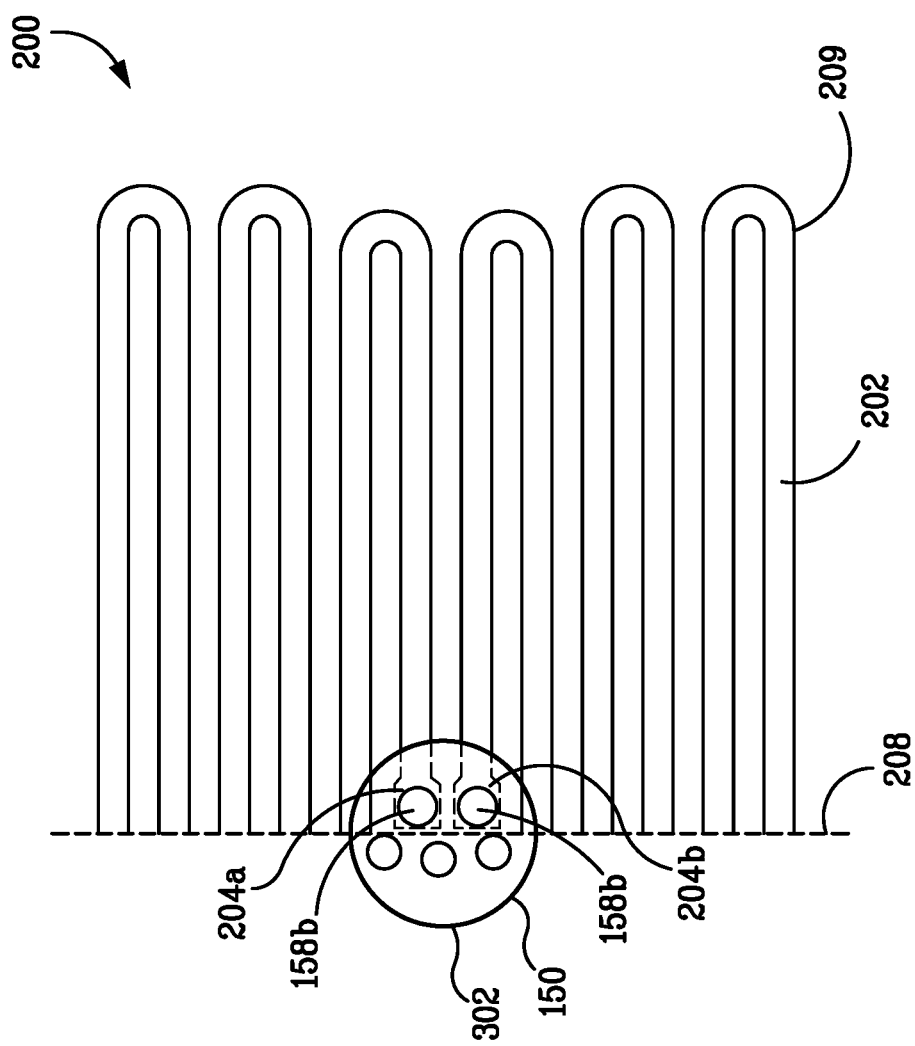
FIG. 6B is a side planar detail view of the electrically resistive heater element shown in FIG. 6A, after having been folded and attached with an adapter element such as shown in FIG. 5A, in accordance with an embodiment of the disclosure.

Referring to FIG. 5B, in various embodiments, the second set of pins 164 may instead cooperate with contact pads or electrical connectors 158*b*' on the face 375 of the middle piece 302, which may be utilized when electrically connecting a heater 200 such as shown in FIG. 6B.

Referring now to FIGS. 5B and 5E, in various embodiments, the middle piece 302 may be provided with a plurality of apertures (ports) 390, 392, 394 for directing fluid flow into and from the interior 118 of the device compartment bag 112 via the port 154*b* provided in the second end piece 304. In some embodiments, the middle piece 302 may be provided with a body of fibrous material 400 to absorb or otherwise catch lingering atomized therapeutic agent when a vacuum is drawn through the port 154*b* of the second end piece 304 via the apertures 390, 392, 394 of the middle piece 302.

Referring particularly to FIG. 5G, in some embodiments, a crescent shaped filter 402 may be contained within the second end piece 304 in a superposed relation to the port 154*b* to remove bacteria, particles and other contaminants when a positive flow of air is directed through the port 154*b* into the middle piece 302 (instead of a vacuum being drawn therethrough). The filter material may comprise commercially available 0.2-micron bacterial filter material.

In various embodiments the accessory 116 may have the capacity to both draw vacuum and to introduce a positive airflow into the device compartment bag 112 through the port 154*b* of the second end piece 304 and the apertures 390, 392, 394 of the middle piece 302. In some embodiments, a vacuum pump 136 of the accessory 116 may be reversible so as to have the capacity to draw vacuum and to generate a positive airflow under the command of the controller 32' of the accessory 116. In other embodiments, a single pump may cooperate with two or more valves so as to establish a capacity to establish opposite flow directions on command. In many embodiments, the positive flow may flush atomized therapeutic agent from the fibrous absorbent body 400 within the middle piece 302 and blow atomized therapeutic agent from within the space 399 of the middle piece 302 positively into the interior 118 of the device compartment bag 112. In most instances, the positive flow inflates the bag 112 and helps circulate atomized therapeutic agent about the object to be coated 22 within the bag 112.

It is to be realized that the adapter 150 may be constructed differently from that which is specifically shown and described with references to FIGS. 5A-G. For example, the nebulizer 28, together with the requisite electrical connectors, might be located in a modified middle piece 302 instead of the first end piece 300, thereby rendering a two-piece adapter design instead of a three-piece design as disclosed. Other variations and adaptations are perceivable from the teachings herein, all which could provide an adapter which provides the desired functionalities of the disclosed adapter 150, such as providing connection with the bag 112, providing support for the nebulizer 28 and enclosing requisite electrical connections for the nebulizer 28 and other devices within the confines of the adapter so that wiring and the like may not lie in nor be exposed to the interior 118 of the device compartment bag 112.

Referring to FIG. 4F, in an embodiment, the reservoir 18 of the nebulizer 28 may be supported inside of the device compartment bag 112 by the adapter 150. In various embodiments, the reservoir 18 may have the capacity to hold approximately 2 cc of therapeutic solution.

As previously mentioned, the adapters 152, 150 may be provided with additional electrical connectors, such as electrical connectors 158*a*, 158*b*, respectively, to provide electrical connection for additional devices such as a resistive heater 200 shown in FIG. 6B. In some embodiments, a resistive heater 200 might be operated under the direction of the controller 32' to promote or otherwise accelerate drying of a coat of deposited therapeutic agent or to serve as a thermal driver to volatilize a therapeutic agent or other agent from a substrate. A resistive heater 200 may also be operated to elevate the temperature of atomized therapeutic agent within the device compartment bag 112 to promote deposition of the therapeutic agent upon the object to be coated 22.

Referring now specifically to FIGS. 6A and 6B, in some embodiments, the resistive heater 200 may be constructed from a serpentine electrically resistive foil 202, which may be a flexible electrical heating element comprised of an aluminum/PET laminate in this example, supported upon the flexible (outer) wall 117 of the device compartment bag 112. In various embodiments, the serpentine resistive foil 202 may be provided with electrical terminals 204*a*, 204*b* which may be in the form of tabs to which the ends of the pins 164 of the electrical connectors 158*b* may be contacted or attached. In the context of the embodiment shown and described with reference to FIG. 5A-G, an edge portion of the resistive heater 200 may be interposed and clamped between the middle piece 302 and the second end piece 304, with the ends of the pins 164 of the connectors 158*b* bearing against the terminals 204*a*, 204*b* of the resistive heater 200. Alternatively, an edge portion of the resistive heater 200 may be interposed and clamped between the first end piece 300 and the middle piece 302, wherein the pins 164 will of the connectors 158*b* may extend to and bear against the terminals 204*a*, 204*b* at or about the locations of the receivers 386, 388 in FIG. 5C.

In constructing the resistive heater 200, the serpentine foil 202 may be sufficiently robust to be free standing or may be first established upon a PET or polyimide substrate 209, and then folded along a central transverse fold line 208. The serpentine foil 202 may be constructed from a suitable aluminum alloy and/or a suitable copper alloy Referring now to FIG. 4F, in various embodiments, the flexible walls 117 may be constructed from a flexible heat resistant material such as PET or polyimide, and may include a printed layer of conductive material in the form of the aforementioned serpentine array or other pattern. In various other embodiments, a spacer layer 212 may be interposed between the serpentine heater array 200 and the walls 117 of the device compartment bag 112, which may provide thermal and electrical insulation between the heater array 200 and adjacent portions of the flexible walls 117. The spacer layer 212 may comprise a polymeric mesh constructed from materials which are well-known in the art, such as a polypropylene mesh.

The device compartment bag 112 may further comprise a second, inner spacer layer 212 which may be constructed from a layer of polypropylene mesh or other polymeric mesh. In various embodiments, the inner spacer layer 212 may help prevent the outer walls 117 from collapsing directly against the object to be coated 22 and may help assure exposure of outer surfaces of the object 22 within a sealed compartment bag 112 to the atomized therapeutic agent as established by the operation of the nebulizer 28 or other atomizing device. In some embodiments, the spacer 212 may provide about 0.5 to 2 mm of spacing. Generally, the spacer layer 212 may provide some degree of conformal open space for transport of aerosol, mist, vapor, fog or cloud of atomized therapeutic agent produced by the nebulizer 28 in the device chamber 15. In various embodiments, the spacer layer 212 may be supplemented or replaced with other spacing expedients such as plastic ribbing or the like.

Referring now to FIG. 4E, in various embodiments, a single spacer layer 212 may be disposed within the device compartment bag 112 and may be clamped in place between two of the pieces 300, 302, 304 of the adapter 150.

The source of electrical power 133 of the accessory 116 may comprise one or more batteries 133 and/or a plug-in connector for connection with an electrical wall socket 133'.

In the description which follows regarding the method of applying a therapeutic agent during a surgical operation as shown in FIGS. 7A-H, the embodiment used in those figures correspond with the embodiments shown in FIG. 4D, wherein a nebulizer 28 extends outwardly from the exposed side 350 of the first end piece 300 of the adapter 150. In this embodiment, the ribbed seal 119 is located away and below the adapter 150. It is to be understood that embodiments shown in FIG. 4F and others, which may include a resistive heater 200 and may have its ribbed seal 119 located at an opposite (upper) end portion of the device compartment bag 112, may also be readily utilized to execute the method shown in FIGS. 7A-H, in accordance with the teachings which follow.

Figure 7A:
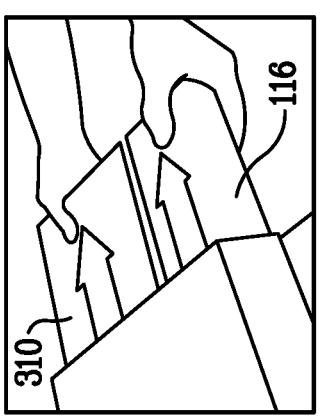
Figure 7B:
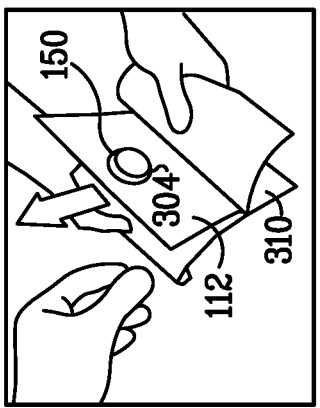
Figure 7C:
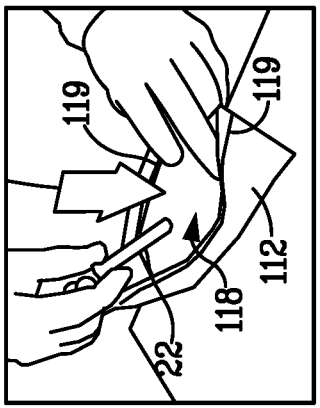
Figure 7D:
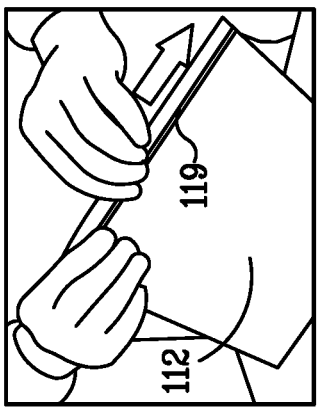
Figure 7E:
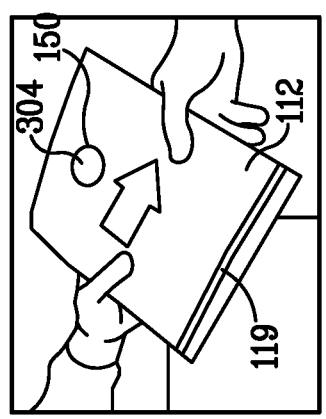
Figure 7F:
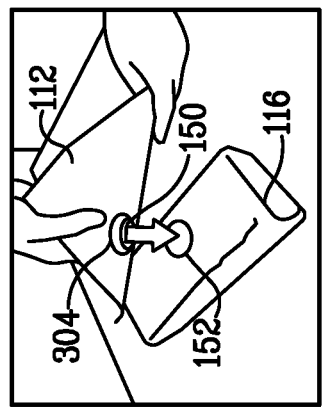
Figure 7G:
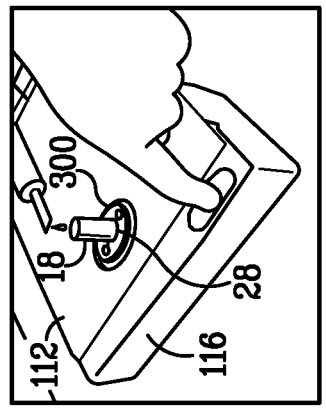
Figure 7H:
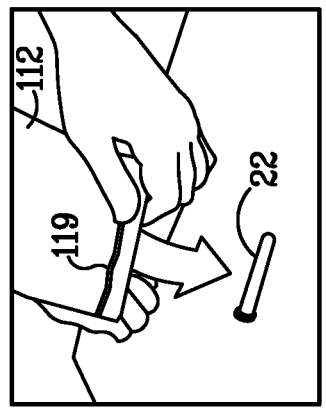

Referring now to FIGS. 7A-H for those embodiments comprising a device compartment bag 112 and an accessory unit 116, a method of applying a therapeutic agent to a surgical object 22 such as a surgical implant or surgical instrument may be practiced by conducting the following, by way of an example:

retrieving the packet 310 and an accessory 116 from a dispenser 312 and removing the device compartment bag 112 from its packet 310, wherein the latter may be conducted within the sterile field of an operating room (see FIGS. 7A, B);

delivering the device compartment bag 112 to the sterile field of an operating room using standard aseptic transfer techniques and inserting the article to be coated 22 (such as a surgical instrument or a surgical implant) into the device compartment bag 112 (see FIG. 7C);

closing and resealing the device compartment bag 112 (which may be undertaken in the sterile field) (see FIG. 7D);

transferring the sealed device compartment bag 112 out of the sterile field to a location of the accessory unit 116, which may be outside the sterile field (see FIG. 7E);

temporarily attaching the adapter 150 of the sealed device compartment bag 112 to the adapter 152 of the accessory unit 116 (see FIG. 7F);

loading a predetermined amount of therapeutic agent (such as an aqueous solution/suspension of an antibiotic or antimicrobial agent or the like) into the reservoir 18 of the nebulizer 28 with a syringe or dropper or the like (which may be undertaken outside the sterile field) and activating the accessory unit 116 to execute a coating cycle, which may include the following: (see FIG. 7G):

nebulizing the therapeutic agent (for approximately 30 seconds) to form a "fog" within the device compartment bag 112;

drawing vacuum for approximately 2 to 3 minutes inside the sealed device compartment bag 112 to dry the coating and remove lingering therapeutic agent within the device compartment bag 112;

releasing the vacuum;

transferring the coated object 22 within sealed bag 112 to the sterile field of the operating room; and opening the device compartment bag 112 and removing the coated object 22 from the bag 112 within the sterile field (see FIG. 7H).

In various embodiments, the application cycle may start with drawing vacuum through the port 154b followed by a mist generation (operation of the nebulizer 28) and a blowing (directing a positive airflow through the port 154b and into the bag 112 through the ports 90, 92, 94 of the middle piece 302. Such misting and blowing are repeated a desired number of times and each misting and each blowing may have a time span of two seconds each or more and may vary in time span. The repeated misting and blowing may conclude within a time span of approximately 30 seconds to 1.5 minutes or more. A vacuum drying step may then follow as previously described Referring now to FIGS. 8A and 8B, a device compartment bag 112 may be individually packaged in a sterile condition within the confines of an openable, sealed packet ("primary package") 310 to maintain sterility. Multiple packets 310 may be stacked in a dispenser 312 which may be in the form of carton from which individual packets 310 may be withdrawn. The accessory base unit 116 may be affixed to the dispenser 312 and may be removably attachable to any one of the device compartment bags 112 once a packet 310 has been removed from the dispenser 312 and the packet 310 opened. In this embodiment the device compartment bag 112 may be configured for a single use.

The accessory unit 116 may be supported by the same carton dispenser 312 from which the individual packets 310 are housed. The adapter 152 of the accessory unit 116 may be disposed in a manner that facilitates temporary attachment of the device compartment bag 112 to the accessory unit 116 when pressing adapters 152 and 150 together. Requisite electrical power and vacuum may be communicated to the accessory 116 unit via a connection or tether 314 to an external source of power such as an electric wall socket and an external source of vacuum. In various other embodiments, the accessory unit 116 may include its own batteries 316 to drive devices such as a vacuum pump 36 within the accessory unit 116. A controller 32 may also be located within the accessory 116 or instead remotely communicated through the tether 314. The nebulizer 28 may be located within the confines of the device compartment bag 112 or optionally in the accessory unit 116.

Referring now to FIGS. 9A and 9B in another embodiment, the accessory unit 116' may be integrated with the device compartment bag 112 so as to form a unitary complete coating applicator unit 10 that may be disposable after a single use. The accessory portion 116' may be solely battery-powered or solely powered by a connection through a tether 314 to an external electric source such as an electric wall socket or both. In various embodiments, the integrated device compartment bag 112' and accessory 116', together with tether 314 may all be packaged within an individual packet (primary package) 310'. In this and various other embodiments, the vacuum source (pump) 36 may be an external vacuum source 36 which is communicated to the accessory 116' and/or the device compartment bag 112 through the tether 314.

Figure 10:
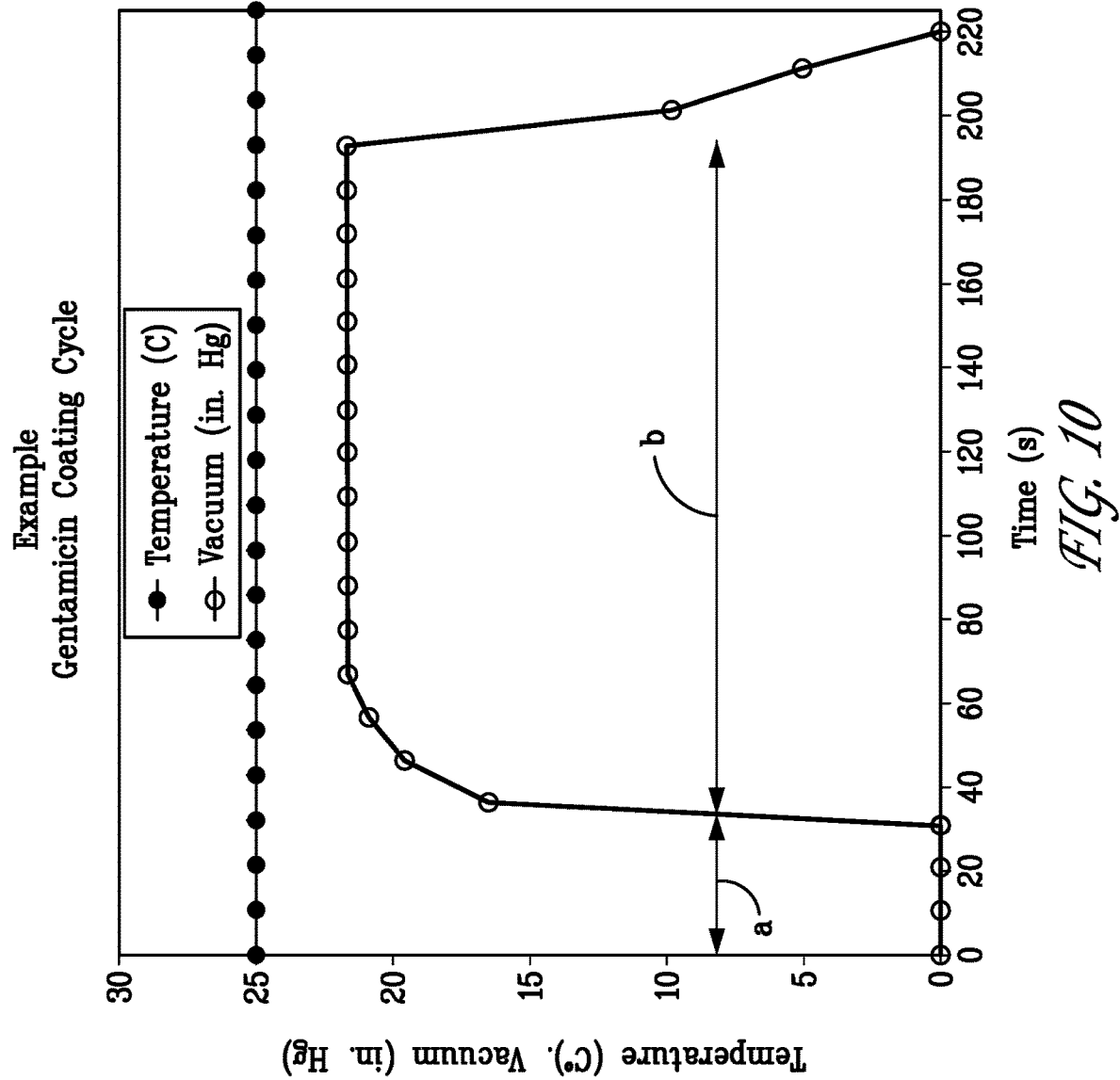

Referring now to FIG. 10, the controller 32 of the base 16 and the accessory 116 may be configured to execute an application cycle which comprises a period in which the nebulizer 28 is turned on to atomize a therapeutic agent and turned off at conclusion of a predetermined period of time or responsive to a measured/monitored condition whereupon the controller initiates operation of the vacuum pump 36 for a prescribed time or until another prescribed condition is detected. In an embodiment, the nebulizer 28 may be turned on for approximately 30 seconds, whereupon the vacuum pump may be operated for approximately 2 to 3 minutes for purposes of evacuating the device compartment 12, 112 and drying the coating of therapeutic agent on the object 22. For surgical implants 22, it may be preferred to dry the implants 22 to a moisture level permitting handling and robust adhesion of the coating. This cycle may be useful in coating a 4% solution of Gentamicin on surgical insert such as surgical screws and plates. If thermal assisted drying is not needed, as represented in FIG. 10, the temperature within the device compartment 12, 112 may remain steady and near ambient during substantially all of the coating cycle.

The Cold Finger Effect

In connection with conducting coating operations with any of the previously described embodiments, coating efficiencies, consistency and other enhancements may be achievable by cooling the object to be coated 22 to a temperature below ambient prior to or while contacting the object 22 with an atomized therapeutic agent in the device compartment 12 (or device compartment bag 112). In some embodiments the object to be coated 22 may be cooled to a temperature in the range of approximately −50° C. to approximately 15° C. prior to contacting the object 22 with an atomized therapeutic agent in the device compartment 12 or bag 112. It is believed that the atomized therapeutic agent may be in most instances at a temperature at or about ambient and that the temperature differential between and the chilled object 22 and the atomized therapeutic agent may help promote and/or accelerate the deposition and/or condensation of the atomized therapeutic agent upon the surface of the chilled object 22. The coating process may be further enhanced by elevating the temperature of the atomized therapeutic agent with a heater such as with the sinusoidal resistive heater element 200 shown and described with reference to FIG. 6B, or by including another form of a resistive heater element that may be communicated with the aerosol, mist, vapor, fog or cloud of atomized therapeutic agent produced by the nebulizer 28 in the device chamber 15. The heating of the atomized therapeutic agent may be utilized either instead of or in addition to the chilling of the object 22.

It is envisioned that the object to be coated 22 may be chilled while in its sterilized packaging in a refrigerator or freezer compartment prior to insertion of the device 22 into a device compartment 12, 112 of the various embodiments. Instead or in addition, the vacuum system 34 may be operated to vacuum chill the object 22 prior to execution of a coating cycle by operating the vacuum system 34 while the device compartment 12 (device compartment bag 112) is loaded with an object 22 and sealed for a time sufficient for the reduction of pressure and temperature within the device compartment 12 (device compartment bag 112) to chill the object 22 to a desired, reduced temperature, whereupon the desired coating cycle would be initiated.

In various embodiments, it may be desirable to limit the rise in temperature of the chilled object 22 to not greater than 15° C. during the time in which the chilled object 22 is contacted with the atomized therapeutic agent. In various embodiments, it may be desirable to limit the contacting to a time period in the range of approximately 1 minute to 15 minutes.

Whether chilling the object 22 and/or elevating the temperature of the atomized therapeutic agent, the deposition of atomized therapeutic agent upon the object 22 may be enhanced if a difference in temperature between the object 22 and the atomized therapeutic agent is in the range of approximately 50 to 100° C. With some therapeutic agents it may be preferable to only heat the atomized therapeutic agent without chilling the object 22.

EXAMPLES

Figure 11:
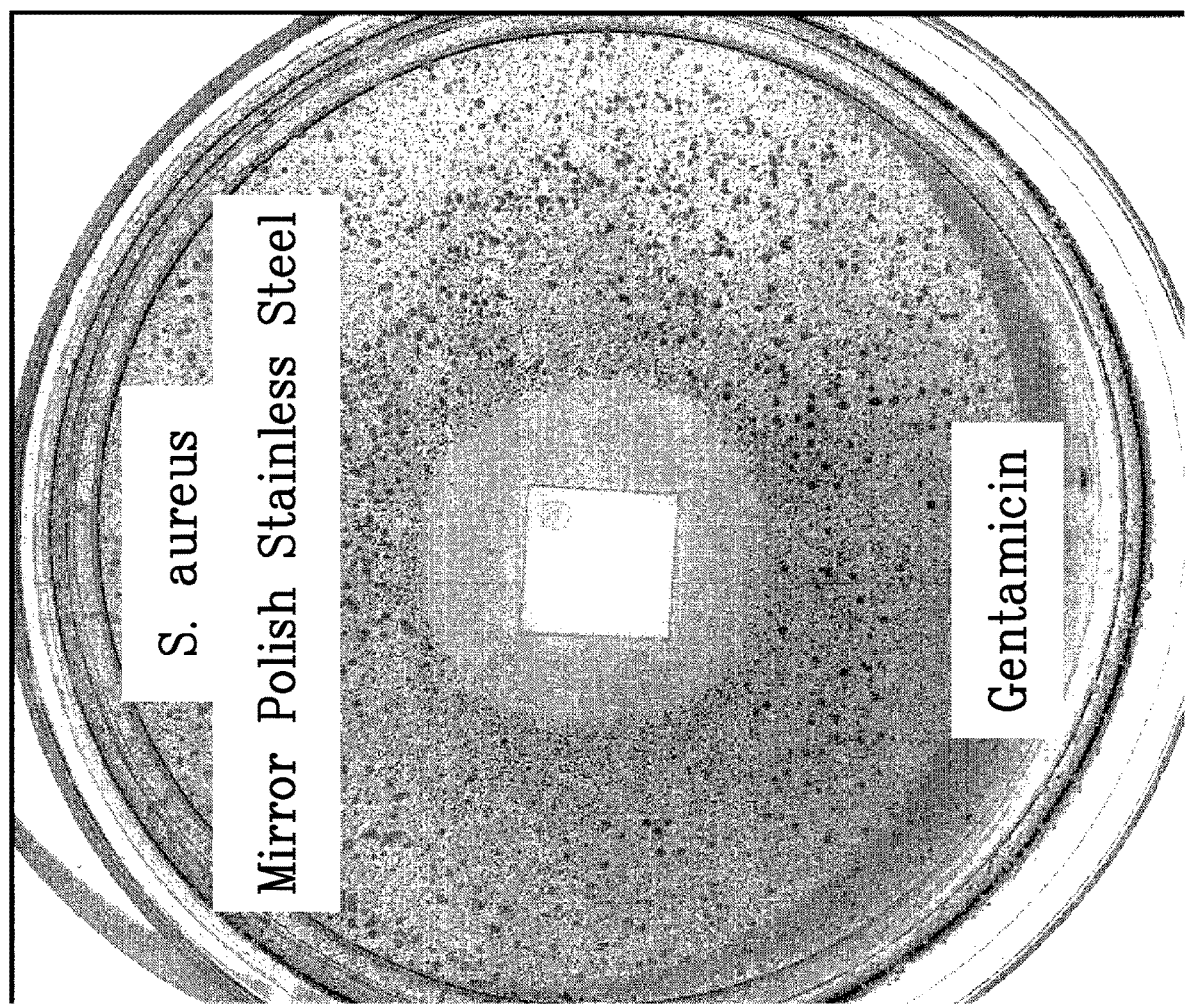

A 4% gentamicin solution in water was applied to a 0.5" polished 316 stainless steel coupon using the device described in FIGS. 3A and 3B according to the cycle described in FIG. 10. The stainless steel coupon was then incubated at 38° C. for 24 hours in an agar plate containing an initial *Staphylococcus aureus* inoculum of $10^5$ bacteria per cubic centimeter of solution. The image shown in FIG. 11 indicates that a protective zone of inhibition of approximately 8 mm was formed around the coupon.

INDUSTRIAL APPLICABILITY

The systems and methods disclosed herein are applicable to the medical device industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and sub-combinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and sub-combinations that are directed to one of the disclosed inventions and are novel and non-obvious. Inventions embodied in other combinations and sub-combinations of features, functions, elements and/ or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

While the present disclosure is being illustrated and described below by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A coating applicator operable to apply a coating of a therapeutic agent upon an object to be coated, comprising:
    an openable and sealable device compartment having a rigid wall;
    a therapeutic agent positioned in communication with the device compartment;
    an atomizer operable to atomize the therapeutic agent, wherein the atomizer comprises an ultrasonic nebulizer and/or a jet nebulizer and/or a vibrating mesh nebulizer and/or a pressurized spray nozzle nebulizer and/or a vibrated frit nebulizer and/or a thermally driven, wick-based aerosol generator and/or a heated capillary aerosol generator and/or a vaporizer;
- a source of vacuum in communication with the device compartment;
- a drier, the drier comprising an arrangement to operate the source of vacuum for a time sufficient to promote drying of the deposited therapeutic agent;
- a base comprising a first connection operable to communicate the source of vacuum with the device compartment and a second connection operable to communicate a source of electrical power to the device compartment for operating the atomizer; and
- a vacuum lid removably and sealably connectable to the base, whereby a sealed space is established about the device compartment,
- wherein the device compartment comprises an openable box configured for placement within the sealed space, the openable box comprising:
  - a support for the object to be coated;
  - a first receiver for receiving the first connection of the base; and
  - a second receiver for receiving the second connection of the base.

2. The coating applicator of claim 1, wherein the device compartment is openable and sealable with a vacuum lid.

3. The coating applicator of claim 1, wherein the drier further comprises an arrangement to apply heat in a region of the device compartment.

4. The coating applicator of claim 1, wherein the drier further comprises an arrangement to communicate heat released from a chemical reaction.

5. The coating applicator of claim 1, wherein the object is a surgical implant and/or a medical device.

6. The coating applicator of claim 1, wherein the therapeutic agent is contained in a reservoir, the reservoir being Tillable from a dispensing device.

7. The coating applicator of claim 1, wherein the atomizer comprises a nebulizer.

8. The coating applicator of claim 1, wherein the therapeutic agent comprises a liquid.

9. The coating applicator of claim 8, wherein the therapeutic agent comprises a suspension and/or an emulsion and/or a solution.

10. The coating applicator of claim 1, wherein the base is configured to receive edge portions of the vacuum lid, and wherein the device compartment comprises:
- a seal operative between the base and edge portions of the vacuum lid;
- wherein the base provides support for the source of vacuum, the atomizer and the object to be coated.

11. The coating applicator of claim 1, wherein the atomizer is disposed wholly within the openable box.

12. The coating applicator of claim 1, wherein the flexible wall comprises:
- a flexible outer wall;
- a planar heating element;
- a planar first spacer disposed between the flexible outer wall and the planar heating element; and
- a planar second spacer disposed between the planar heating element and an interior of the device compartment.

13. The coating applicator of claim 12, wherein the first and second planar spacers comprise a mesh.

14. The coating applicator of claim 12, wherein the heater comprises a serpentine heater.

15. The coating applicator of claim 1, wherein the atomizer comprises an ultrasonic nebulizer and/or a vibrating mesh nebulizer.

16. A coating applicator operable to apply a coating of a therapeutic agent upon an object to be coated, comprising:
- an openable and sealable device compartment openable and sealable along a first end portion and having a flexible wall;
- a therapeutic agent positioned in communication with the device compartment;
- an atomizer operable to atomize the therapeutic agent, wherein the atomizer comprises an ultrasonic nebulizer and/or a jet nebulizer and/or a vibrating mesh nebulizer and/or a pressurized spray nozzle nebulizer and/or a vibrated frit nebulizer and/or a thermally driven, wick-based aerosol generator and/or a heated capillary aerosol generator and/or a vaporizer;
- a source of vacuum in communication with the device compartment; and
- an accessory unit operable to communicate the source of vacuum with the device compartment, the accessory unit being further operable to connect a source of electrical power with the atomizer.

17. The coating applicator of claim 16, wherein the vacuum source is fluidly communicated with the device compartment at a location spaced from the first end portion.

18. The coating applicator of claim 16, wherein the vacuum source is fluidly communicated with the device compartment at a location adjacent the first end portion.

19. The coating applicator of claim 16, wherein the atomizer is disposed wholly within the device compartment.

20. The coating applicator of claim 16, further comprising a tether operable to remotely connect the accessory unit with the device compartment, whereby the device compartment may remain in a sterile field of an operating room while the accessory unit is operated at another location in the operating room.

21. The coating applicator of claim 16, wherein the accessory unit is integrated with a single device chamber.

22. The coating applicator of claim 16, further comprising a plurality of discrete device compartments, the accessory unit being repetitively attachable with different members of the plurality of discrete device compartments.

23. The coating applicator of claim 16, further comprising a tether operable to remotely connect the accessory unit with an external source of vacuum and/or connect the accessory unit with an external source of electrical power, whereby the device compartment and the accessory unit may remain in a sterile field of an operating room during their operation.

* * * * *